US011535861B2

(12) United States Patent
Lepeltier et al.

(10) Patent No.: US 11,535,861 B2
(45) Date of Patent: Dec. 27, 2022

(54) TOMATO PLANT RESISTANT TO TOMATO YELLOW LEAF CURL VIRUS, POWDERY MILDEW, AND NEMATODES

(71) Applicant: VILMORIN & CIE, Paris (FR)

(72) Inventors: Jean-Christophe Lepeltier, Saint Rémy de Provence (FR); Eric Lionneton, La Bohalle (FR); Jean-Claude Mercier, Avignon (FR)

(73) Assignee: VILMORIN & CIE, Paris (FR)

( * ) Notice: Subject to any disclaimer, the term of this patent is extended or adjusted under 35 U.S.C. 154(b) by 82 days.

(21) Appl. No.: 16/617,376

(22) PCT Filed: May 31, 2018

(86) PCT No.: PCT/EP2018/064370
§ 371 (c)(1),
(2) Date: Nov. 26, 2019

(87) PCT Pub. No.: WO2018/220136
PCT Pub. Date: Dec. 6, 2018

(65) Prior Publication Data
US 2021/0123070 A1    Apr. 29, 2021

(30) Foreign Application Priority Data
May 31, 2017    (EP) .................................... 17305641

(51) Int. Cl.
| | | |
|---|---|---|
| *A01H 5/08* | (2018.01) | |
| *A01H 1/04* | (2006.01) | |
| *C12N 15/82* | (2006.01) | |
| *A01H 6/82* | (2018.01) | |
| *C12Q 1/6895* | (2018.01) | |

(52) U.S. Cl.
CPC ........... *C12N 15/8283* (2013.01); *A01H 1/04* (2013.01); *A01H 5/08* (2013.01); *A01H 6/825* (2018.05); *C12N 15/8282* (2013.01); *C12N 15/8285* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS 7,615,689 B2    11/2009    Hoogstraten et al.

FOREIGN PATENT DOCUMENTS

EP    1563727 A1    8/2005

OTHER PUBLICATIONS

Communication (International Search Report) issued by the International Search Authority in International Application No. PCT/EP2018/064370 dated Jun. 29, 2018, 7 pages total.
Communication (Extended European Search Report) issued by the European Patent Office in European Application No. 17305641.7 dated Sep. 14, 2017, 9 pages total.
Bai, Y. et al., "Tomato Defense to Oidium Neolycopersici: Dominant OI Genes Confer Isolate-Dependent Resistance via a Different Mechanism Than Revessive ol-2" MPMI (2005) vol. 18, No. 4, pp. 354-362.
Garcia, B.E. et al., "A Co-Dominant SCAR Marker, Mi23, for Detection of the Mi-1.2 Gene for Resistance to Root-Knot Nematode in Tomato Germplasm" 2007, 13 pages total.
Lee, J. M. et al., "Molecular Markers for Selecting Diverse Disease Resistances in Tomato Breeding Programs" Plant Breed. Biotech. (2015) vol. 3, No. 4, pp. 308-322.
Seifi, A. et al., "Linked, if Not the Same, Mi-1 Homologues Confer Resistance to Tomato Powdery Mildew and Root-Knot Nematodes" MPMI (2011) vol. 24, No. 4, pp. 441-450.
Seifi, A. et al., "Genetics and Molecular Mechanisms of Resistance to Powdery Mildews in Tomato (*Solanum lycopersicum*) and its Wild Relatives" European Journal of Plant Pathology (2014) vol. 138, No. 3, pp. 641-665.
Noe Fernandez-Pozo, The Sol Genomics Network (SGN)—from genotype to phenotype to breeding, Nucleic Acids Research, 2015, vol. 43, Database issue, Published online Nov. 26, 2014, D1036-D1041, doi: 10.1093/nar/gku1195.

*Primary Examiner* — Phuong T Bui
(74) *Attorney, Agent, or Firm* — Troutman Pepper Hamilton Sanders LLP

(57) ABSTRACT

The present invention relates to *Solanum lycopersicum* (*S. lycopersicum*) plants with resistance to Tomato Yellow Leaf Curl Virus (TYLCV), powdery mildew (PM) and nematodes. According to the invention, the resistances are provided by coupling in cis on the same chromosome the OL4 gene conferring resistance to PM and nematodes and TY1 gene conferring resistance to TYLCV, without coupling the Mi-1 gene conferring resistance to nematodes in cis with said OL4 gene conferring resistance to PM and nematodes and TY1 gene conferring resistance to TYLCV. The genes can be present homozygously or heterozygously in the genome of the *S. lycopersicum* plants, and they confer resistance to TYLCV, PM and nematodes. The present invention also provides methods for making such plants, and to methods of detecting and/or selecting such plants.

12 Claims, 4 Drawing Sheets

Specification includes a Sequence Listing.

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
gaaatcgcag agtcacactt                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse primer -continued

```
<400> SEQUENCE: 2
atcccgtgta attaatcgaa                                                  20

<210> SEQ ID NO 3
<211> LENGTH: 640
<212> TYPE: DNA
<213> ORGANISM: Solanum lycopersicum
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (247)..(247)
<223> OTHER INFORMATION: SNP: if r is a = resistant allele, if r is g =
      susceptible allele

<400> SEQUENCE: 3
ctacgccaca gttnaaangt atgaatatga tctccacaay aaggtttcrt tagaatggct      60
gctggctcta ggtccaagct tgggtattac tcgagtccct ggcatyggcc tygtattcac    120
tgatttgact tctgggattc cagcmaactt ctcacgtttt gttacgaayc tccctgccta    180
ccaccggata cttgttttcg tgtgtgtgaa atcsgtgcct gtccttttg ttcccccagc     240 tgagagrtac ctcgtaggmc gtgttggtcc tgcagctcat cgttcctata gatgcattgt    300
ccgttatggt taccgtgatg ttcaycagga tgttgactcc tttgaatccg aacttgtcag    360
taggctggct gatttcatcc ggtatgattg gtacaaggca catggaatsa tggagacatg    420
caacgaggat gactgctcac gttctggtgc atcgtcagga gaatgtagac tgaccgttat    480
aggaactcta gatttgtcak gcgcaccagc ttttgaagtc gamgaaacca tgcagcctgc    540
aagcgtgtct gtsggktttc ctacagttga aagtgtaacr gatgtgatag agatgcaagc    600
agtggaaaga agggtgagat ttgcgataga tgacgagtcg                          640

<210> SEQ ID NO 4
<211> LENGTH: 42
<212> TYPE: DNA
<213> ORGANISM: Artificial Sequence
<220> FEATURE:
<223> OTHER INFORMATION: Forward primer A1

<400> SEQUENCE: 4
gaaggtgacc aagttcatgc ttttgttccc ccagctgaga gg                        42

<210> SEQ ID NO 5
<211> LENGTH: 44
<212> TYPE: DNA
<213> ORGANISM: Artificial Sequence
<220> FEATURE:
<223> OTHER INFORMATION: Forward primer A2

<400> SEQUENCE: 5
gaaggtcgga gtcaacggat tcttttgttc ccccagctga gaga                      44

<210> SEQ ID NO 6
<211> LENGTH: 22
<212> TYPE: DNA
<213> ORGANISM: Artificial Sequence
<220> FEATURE:
<223> OTHER INFORMATION: Common reverse primer C
```

```
<400> SEQUENCE: 6
gaccaacacg kcctacgagg ta                                              22

<210> SEQ ID NO 7
<211> LENGTH: 22
<212> TYPE: DNA
<213> ORGANISM: Artificial Sequence
<220> FEATURE:
<223> OTHER INFORMATION: Forward primer

<400> SEQUENCE: 7
agctatcagc tgccagagac at                                              22

<210> SEQ ID NO 8
<211> LENGTH: 23
<212> TYPE: DNA
<213> ORGANISM: Artificial Sequence
<220> FEATURE:
<223> OTHER INFORMATION: Reverse primer

<400> SEQUENCE: 8
caccatcatt gtatccagag agc                                             23

<210> SEQ ID NO 9
<211> LENGTH: 265
<212> TYPE: DNA
<213> ORGANISM: Solanum lycopersicum
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (88)..(88)
<223> OTHER INFORMATION: SNP: if s is g = resistant allele, if s is c =
      susceptible allele
<220> FEATURE:
<221> NAME/KEY: misc_feature
<222> LOCATION: (120)..(121)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t

<400> SEQUENCE: 9
tggcaggttc ttacaycttt tnactgttct aaaaagatgt ctacaattyg tttsatcaaa     60
gccccgacgg aactattaag tagacgasgt tagtaaaata acaagcaacc aaakcagttn    120
ngagagatca cttttttccc angggatttt tctagtaaga ttttaaycar gcawattatc    180
twctaaatat rtagcgagtt agtatcatta tactttgtst acaaattaaa tttcgattac    240
tctgggtaaa caagccatat agtat                                         265

<210> SEQ ID NO 10
<211> LENGTH: 45
<212> TYPE: DNA
<213> ORGANISM: Artificial Sequence
<220> FEATURE:
<223> OTHER INFORMATION: Forward primer A2

<400> SEQUENCE: 10
gaaggtcgga gtcaacggat tcgacggaac tattaagtag acgag                    45
```

```
<210> SEQ ID NO 11
<211> LENGTH: 45
<212> TYPE: DNA
<213> ORGANISM: Artificial Sequence
<220> FEATURE:
<223> OTHER INFORMATION: Forward primer A1

<400> SEQUENCE: 11
gaaggtgacc aagttcatgc tcgacggaac tattaagtag acgac            45

<210> SEQ ID NO 12
<211> LENGTH: 30
<212> TYPE: DNA
<213> ORGANISM: Artificial Sequence
<220> FEATURE:
<223> OTHER INFORMATION: Common reverse primer C

<400> SEQUENCE: 12
aactgmtttg gttgcttgtt attttactaa                             30
```

TOMATO PLANT RESISTANT TO TOMATO YELLOW LEAF CURL VIRUS, POWDERY MILDEW, AND NEMATODES

CROSS-REFERENCE TO RELATED APPLICATIONS

This is a U.S. national phase application under 35 U.S.C. § 371 of International Patent Application No. PCT/EP2018/064370, filed May 31, 2018, and claims benefit of priority to European Patent Application No. 17305641.7, filed May 31, 2017. The entire contents of these applications are hereby incorporated by reference.

FIELD OF THE INVENTION

The present invention relates to *Solanum lycopersicum* (*S. lycopersicum*) plants with resistance to Tomato Yellow Leaf Curl Virus (TYLCV), powdery mildew (PM) and nematodes. According to the invention, the resistances are provided by coupling in cis on the same chromosome the OL4 gene conferring resistance to PM and nematodes and TY1 gene conferring resistance to TYLCV, without coupling the Mi-1 gene conferring resistance to nematodes in cis with said OL4 and TY1 genes. The OL4 gene conferring resistance to PM and nematodes and TY1 gene conferring resistance to TYLCV can be present homozygously or heterozygously in the genome of the *S. lycopersicum* plants, and they confer resistance to TYLCV, PM and nematodes. The present invention also provides methods for making such plants, and methods of detecting and/or selecting such plants.

BACKGROUND

Many pathogens, such as Tomato Yellow Leaf Curl Virus, *Oidium neolycopersici* (powdery mildew), or nematodes, can colonize cultures of tomato (*Solanum lycopersicum*).

TYLCV is a begomovirus that causes the most destructive disease in tomato. The virus is found all around the world in more than 30 countries or regions that produce tomatoes, such as Africa, Asia, Australia, Central and North America, and East and South of Europe. The virus is transmitted by the whitefly *Bemisia tabaci* and infects the phloem of the plant, thereby inducing severe stunting, reduction of leaf size upward curling of leaves, chlorosis on leaves and flowers, and reduction of fruit production. To date, no resistance has been found in *S. lycopersicum* germplasm, but high levels of resistance have been found in wild tomatoes species. Currently, five genes/loci (i.e. the Ty-genes) coming from different origins are known to confer resistance to TYLCV: the TY1, TY3 and TY4 genes/loci which come from *Solanum chilense*, the TY2 gene/locus which comes from *Solanum habrochaites*, and TY5 which comes from *Solanum peruvianum*. Consequently, to obtain TYLCV resistant cultivated tomatoes, resistance genes have to be introgressed from these wild accessions. However, most of the Ty-genes are all located in gene clusters, like TY1, TY3 and TY4 that are located in the Mi/Cf/Ol-genes cluster in chromosome 6, and TY2 which is located in the 1-2 gene region on chromosome 11.

The TY1 gene/locus, which is a dominant gene, was the first mapped TYLCV resistance locus and is the resistance gene that is most introgressed into cultivated tomatoes. However, the TY1 introgression is generally accompanied by undesired agronomical traits. It has been demonstrated that the TY1 gene is localized on the pericentromeric region of chromosome 6 (Zamir et al., 1994, Theor. Appl. Genet., 88:141-146), and that it is closely linked to the Mi-1 gene conferring resistance to nematodes (Milo, 2001, Tomato Breeders Roundtable, http://www.oardc.ohio-state.edu/tomato/TBRT %202001%20Abstracts.pdf).

Nematodes are roundworms of the Phylum Nematoda that colonize a wide range of economically important host plants, such as tomatoes. Many different genera of nematodes can punctually infect tomato plants but their incidence is generally low. The root-knot nematode, *Meloidogyne* spp., is by far the most widespread, damaging and economically important nematode infecting tomatoes. Fives species of *Meloidogynes* are reported on tomato: *Meloidogyne incognita* (*M. incognita*, the most widespread), *Meloidogyne javanica* (*M. javanica*), *Meloidogyne arenaria* (*M. arenaria*), *Meloidogyne enterolobii* (*M. enterolobii*) and *Meloidogyne hapla* (*M. hapla*). The disease is characterized by the presence of galls or root-knots on infected plants. Symptoms of nematode infection include poor fruit yield, stunted growth, wilting, and susceptibility to other pathogens (Williamson, 1998, Annu. Rev. Phytopathol., 36:277-293). Resistance is mediated by the single dominant gene Mi-1 that is able to confer a resistance to the three *Meloidogynes* species *M. incognita*, *M. javanica*, and *M. arenaria*. Mi-1 belongs to the class of R genes that encode proteins containing nucleotide-bonding site plus leucine-rich repeats (NBS-LRR). In the R gene cluster, it has been identified seven Mi-homologues, but among them only the Mi-1.2 homologue has been shown to be functional and to confer resistance to nematodes (Milligan et al., 1998, Seah et al., 2004, TAG, 108: 1635-1642).

*Oidium neolycopersici* (*O. neolycopersici*) is a fungus responsible for powdery mildew (PM) in tomato in most of the world countries. Morphologically, *O. neolycopersici* can easily be distinguished from another fungus causing PM, *Leveillula taurica* (*L. taurica*), which occurs more in subtropical regions. The mycelium of *L. taurica* grows into the mesophyll of the leaf and is visible on the underside of the leaf, while *O. neolycopersici* mainly grows on the upper side and usually does not penetrate the mesophyll (Lindhout et al., 1994, Euphytica, 72(1-2):43-49). To date, no effective sources of resistance to *O. neolycopersici* have been found in cultivated tomatoes, but several wild resistant accessions have been found to be resistant. More specifically, nine loci conferring resistance to *O. neolycopersici* have been described: OL1 and OL3 loci (which are probably two allelic variants), and the dominant OL5 locus that come respectively from *Solanum habrochaites* G1.1560, G1.1290 and P1247087 and that all map on chromosome 6; the recessive OL2 locus coming from *Solanum lycopersicum* var. *cerasiforms* LA1230 and mapping on chromosome 4; the dominant OL4 locus originating from *Solanum peruvianum* LA2172 and mapping to the short arm of chromosome 6 at the pericentromeric region; the dominant OL6 locus coming from a breeding line with unknown origin and mapping at the same position as OL4 (i.e. thereby suggesting that OL4 and OL6 are allelic variants); Ol-qt/1 which maps in chromosome 6 in the same chromosomal region as OL1, OL3 and OL5; and Ol-qt/2 and Ol-qt/3 that map on chromosome 12 near the Lv gene conferring resistance to *L. taurica* (Seifi et al., 2014, Eur J Plant Pathol, 138:641-665).

Recently, it has been shown that Near Isogenic Lines (NILs) harboring OL4 gene (NIL-Ol-4) and OL6 gene (NIL-Ol-6) but not bearing the Mi-1.2 gene were also resistant to nematodes and aphids and that transient silencing by VIGS (Virus-induced Gene Silencing) using a conserved domain of Mi-1 homologues in these two NILs compromised their resistance to 0. neolycopersici, thereby suggesting that OL4 and OL6 are Mi-1 homologues (Seifi et al., 2011, Molecular Plant-Microbe Interactions, 24(4):441-450).

To date, one patent application describes in tomato the combination in cis of the TY1 gene conferring resistance to TYLCV and Mi-1 gene conferring resistance to nematodes (WO2005/079342). No further combination of genes conferring resistance to nematodes and TYLCV, nor combination of genes conferring resistances to TYLCV, nematodes and PM have been described in the art.

These disease resistance genes in the tomato genome being clustered as opposed to randomly distributed, repulsion linkages can be problematic for tomato breeders who want to combine resistance genes that are closely linked. Doing this becomes extremely difficult when introgressions from wild species overlap and there is recombination suppression (Verlaan et al. The Plant Journal (2011) 68, 1093-1103).

In this respect, suppression of recombination was reported in the F2 populations derived from interspecific crosses between S. lycopersicum and S. peruvianum, which were used for cloning the Mi-1 gene (Kaloshian et al., 1998, Mol. Gen. Genet. 257: 376-385). More recently, Seifi et al. (2011, Molecular Plant-Microbe Interactions, 24(4):441-450) reported absence of recombination events between 01-4 and an interval flanked by markers 32.5Cla and REX-1, where the Mi-1 gene is located.

Moreover, it is commonly known by breeders that resistance genes (R-genes), such as the Mi-1 resistance gene, may often be ineffective after their introgression into plants because of the rapid genetic evolution of pathogens that allows them to bypass the introgressed resistance. In fact, evolution of pathogens involves the emergence of new virulence genes that prevent the recognition by the host and bypass the resistance of the host. Consequently the existing resistance genes are not able anymore to protect the plant against the new virulence genes leading to the re-emergence of the disease caused by the pathogen. In order to restore the resistance in the plants, it is thus needed to introgressed new combination of resistance genes.

There is thus a need to find and to introgress in tomato alternative combination of genes being able to confer resistances to TYLCV and nematodes than those already present in the art, and also to provide plant further harboring a resistance to PM.

BRIEF SUMMARY OF THE INVENTION

The inventors have been able to combine in cis on the same chromosome the OL4 gene conferring resistance to PM and nematodes and the TY1 gene conferring resistance to TYLCV, without keeping in cis the Mi-1 gene conferring resistance to nematodes, while maintaining a resistance to nematodes. Indeed, for combining in cis resistance genes, such as the resistance OL4 and TY1 genes, without keeping the Mi-1 gene conferring resistance to nematodes, the inventors were faced with the problem that (i) the TY1 gene and Mi-1 gene were known to be genetically close on chromosome 6, and that the TY1, Mi-1 and OL4 genes are all localized in the pericentrometic region of chromosome 6, i.e. a region where the recombination rate is very low. The inventors have thus been able to identify the right recombination event allowing combining the resistance TY1 and OL4 genes without keeping the resistance Mi-1 gene in cis, and thus to obtain a S. lycopersicum plant that is resistant to TYLCV and PM but also to nematodes, even with the absence of the resistance Mi-1 gene.

Thus, in a first aspect, the present invention provides a Solanum lycopersicum (S. lycopersicum) plant that is resistant to Tomato Yellow Leaf Curl Virus (TYLCV), powdery mildew (PM) and nematodes, wherein said plant comprises the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6.

In some embodiments, said OL4 gene conferring resistance to PM and nematodes is identified by SSR-OL4 marker detection.

In some embodiments, said TY1 gene conferring resistance to TYLCV is identified by TO-0178067 and/or TY3-M3 marker detection.

In some embodiments, the presence or absence of Mi-1 gene conferring resistance to nematodes is identified by Mi2.3 marker detection.

In some embodiments, said combination of the resistance genes OL4 and TY1 in coupling phase on chromosome 6, without keeping the resistance gene Mi-1 in said coupling phase, is as found in the genome of the plant TCR1, a representative sample of seed of which has been deposited under NCIMB 42490.

In some embodiments, said plant is the plant TCR1, a representative sample of seed of which has been deposited under NCIMB 42490, or said plant is a plant having all of the morphological and physiological characteristics of the plant TCR1.

Also provided is an isolated cell of the S. lycopersicum plant according to the invention.

Further provided is a plant part obtained from a S. lycopersicum plant according to the invention. In some embodiments, said plant part is a seed, a fruit, in particular a parthenocarpic fruit, a reproductive material, roots, flowers, a rootstock or a scion.

The present invention also provides a seed of a S. lycopersicum plant, giving rise when grown up to a plant according to the invention.

Also provided is a hybrid plant of a S. lycopersicum, which is resistant to Tomato Yellow Leaf Curl Virus (TYLCV), powdery mildew (PM) and nematodes, obtainable by crossing a S. lycopersicum plant with a resistant plant according to the invention.

Also provided is a container comprising a plant, a plant part, a seed or a hybrid plant according to the invention.

Further provided is a method for detecting and/or selecting a S. lycopersicum plant that is resistant to Tomato Yellow Leaf Curl Virus (TYLCV), powdery mildew (PM) and nematodes, wherein said method comprises:
  a) detecting the presence or absence of:
    OL4 gene conferring resistance to PM and nematodes, said OL4 gene being identified by SSR-OL4 marker detection,
    TY1 gene conferring resistance to TYLCV, said TY1 gene being identified by TO-0178067 and/or TY3-M3 marker detection, and
    Mi-1 gene conferring resistance to nematodes, said Mi-1 gene being identified by Mi2.3 marker detection; and
  b) selecting as a plant resistant to TYLCV, PM and nematodes, the S. lycopersicum plant in which the OL4 gene conferring resistance to PM and nematodes and TY1 gene conferring resistance to TYLCV have been detected as present in coupling phase on chromosome 6 and the Mi-1 gene conferring resistance to nematodes has been detected as absent in said coupling phase.

The present invention also provides the use of the *S. lycopersicum* resistant plant according to the invention as a breeding partner in a breeding program for obtaining *S. lycopersicum* plant resistant to Tomato Yellow Leaf Curl Virus (TYLCV), powdery mildew (PM) and nematodes.

Also provided are methods for producing *S. lycopersicum* seed. In some embodiments, the methods comprise crossing the *S. lycopersicum* plant according to the invention with itself or with another *S. lycopersicum* plant, and harvesting the resultant seed.

Further provided is a method for improving the yield of *S. lycopersicum* plants in an environment infested by at least one pathogen selected from the group consisting of Tomato Yellow Leaf Curl Virus (TYLCV), powdery mildew (PM) and nematodes, comprising growing *S. lycopersicum* plants resistant to Tomato Yellow Leaf Curl Virus (TYLCV), powdery mildew (PM) and nematodes wherein said plant comprises the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6.

Also provided is a method for improving the yield of *S. lycopersicum* plants in an environment infested by at least one pathogen selected from the group consisting of Tomato Yellow Leaf Curl Virus (TYLCV), powdery mildew (PM) and nematodes comprising:
  a) identifying *S. lycopersicum* plants resistant to Tomato Yellow Leaf Curl Virus (TYLCV), powdery mildew (PM) and nematodes comprising the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6, and
  b) growing said *S. lycopersicum* resistant plants in said infested environment.

Also provided is a method for protecting a field from infestation and/or spread at least one pathogen selected from the group consisting of Tomato Yellow Leaf Curl Virus (TYLCV), powdery mildew (PM) and nematodes, comprising growing *S. lycopersicum* plants resistant to Tomato Yellow Leaf Curl Virus (TYLCV), powdery mildew (PM) and nematodes which comprise the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6.

Further provided is a method for increasing the number of harvestable or viable *S. lycopersicum* plants in an environment infested by at least one pathogen selected from the group consisting of Tomato Yellow Leaf Curl Virus (TYLCV), powdery mildew (PM) and nematodes, comprising growing *S. lycopersicum* plants resistant to Tomato Yellow Leaf Curl Virus (TYLCV), powdery mildew (PM) and nematodes which comprise the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6.

The use of a *S. lycopersicum* plant resistant to Tomato Yellow Leaf Curl Virus (TYLCV), powdery mildew (PM) and nematodes which comprises the (i) OL4 gene conferring resistance to PM and nematodes, and (ii) TY1 gene conferring resistance to TYLCV, in coupling phase on chromosome 6, and wherein said plant does not comprises the Mi-1 gene conferring resistance to nematodes in said coupling phase on chromosome 6, for controlling infestation in a field by at least one pathogen selected from the group consisting of Tomato Yellow Leaf Curl Virus (TYLCV), powdery mildew (PM) and nematodes is further provided.

Further provided is a method for the production of *S. lycopersicum* plantlets or plants resistant to Tomato Yellow Leaf Curl Virus (TYLCV), powdery mildew (PM) and nematodes, which method comprises:
  a) culturing in vitro an isolated cell or tissue of the *S. lycopersicum* plant according to the invention to produce *S. lycopersicum* micro-plantlets resistant to Tomato Yellow Leaf Curl Virus (TYLCV), powdery mildew (PM) and nematodes, and
  b) optionally further subjecting the *S. lycopersicum* micro-plantlets to an in vivo culture phase to develop into *S. lycopersicum* plant resistant to Tomato Yellow Leaf Curl Virus (TYLCV), powdery mildew (PM) and nematodes.

Definitions

As used herein, the term "plant part" refers to any part of a plant including but not limited to the shoot, root, stem, seeds, fruits, leaves, petals, flowers, ovules, branches, petioles, internodes, pollen, stamen, rootstock, scion and the like.

The term "resistance" is as defined by the ISF (International Seed Federation) Vegetable and Ornamental Crops Section for describing the reaction of plants to pests or pathogens, and abiotic stresses for the Vegetable Seed Industry.

Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

By "tolerance", it is meant the ability of a plant variety to endure biotic and abiotic stress without serious consequences for growth, appearance and yield.

As used herein, the term "susceptible" refers to a plant that is unable to restrict the growth and development of a specified pest or pathogen.

As used herein, the term "offspring" or "progeny" refers to any plant resulting as progeny from a vegetative or sexual reproduction from one or more parent plants or descendants thereof. For instance, an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of a second generation (F2) or subsequent generations (F3, F4, etc.) are specimens produced from selfing of F1's, F2s, etc. An F1 may thus be (and usually) a hybrid resulting from a cross between two true breeding parents (true-breeding is homozygous for a trait), while an F2 may be (and usually is) an offspring resulting from self-pollination of said F1 hybrids.

As used herein, the term "cross", "crossing" refer to the process by which the pollen of one flower on one plant is applied (artificially or naturally) to the ovule (stigma) of a flower on another plant.

As used herein, the term "heterozygote" refers to a diploid or polyploidy cell or plant having different alleles (forms of a given gene or sequences) present at least one locus.

As used herein, the term "heterozygous" refers to the presence of different alleles (forms of a given gene or sequences) at a particular locus.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "line" refers to a relatively true-breeding strain.

As used herein, the term "Phenotype" refers to the observable characters of an individual cell, cell culture, organism (e.g. a plant), or group of organisms which results from the interaction between that individual genetic makeup (i.e. genotype) and the environment.

As used herein, the terms "in coupling phase" or "in cis" refer to a genetic condition in which the alleles of two different loci are physically located on the same chromosome and inherited together. For example, when the OL4 and TY1 alleles conferring resistance to PM, nematodes and TYLCV are located on the same homologous chromosome, these alleles are said to be "in coupling phase". In contrast, when the OL4 and TY1 alleles conferring resistance to PM, nematodes and TYLCV are located on different homologous chromosomes, these alleles are said to be "in repulsion phase" or "in trans".

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may be optionally be completed by backcrossing to the recurrent parent, in which case introgression refers to infiltration of the genes of one species into the gene pool of another through repeated backcrossing of an interspecific hybrid with one of its parents. An introgression may be also described as a heterologous genetic material stably integrated in the genome of a recipient plant.

As used herein, the terms "molecular marker" refer to an indicator that is used in methods for visualizing differences in characteristics of nucleic acid sequences. Examples of such indicators are restriction fragment length polymorphism (RFLP) markers, amplification fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the person skilled in the art using common molecular techniques.

As used herein, the term "primer" refers to an oligonucleotide which is capable of annealing to the amplification target allowing a DNA polymerase to attach, thereby serving as a point of initiation of DNA synthesis when placed under conditions in which synthesis of primers extension product is induced, i.e., in the presence of nucleotides and an agent for polymerization such as DNA polymerase and at a suitable temperature and pH. The primer is preferably single stranded for maximum efficiency in amplification. Preferably, the primer is an oligodeoxyribonucleotide. The primer must be sufficiently long to prime the synthesis of extension products in the presence of the agent for polymerization. The exact length of the primers will depend on many factors, including temperature and composition (A/T and G/C content) of primer. A pair of primers consists of one forward and one reverse primer as commonly used in the art of DNA amplification such as in PCR amplification.

By "Tomato Yellow Leaf Curl Virus" or "TYLCV", it is meant a begomovirus that causes the yellow leaf curl disease in tomato. The virus is transmitted by the whitefly *Bemisia tabaci* and infects the phloem of the plant, thereby inducing severe stunting, reduction of leaf size upward curling of leaves, chlorosis on leaves and flowers, and reduction of fruit production.

By "powdery mildew" or "PM", it is meant a fungal disease caused by fungi of the order Erisyphales. In the context of the present application, powdery mildew is caused by *Oidium neolycopersici* (*O. neolycopersici*). Symptoms of powdery mildew caused by *O. neolycopersici* appear as white and powdery spots on the upper surface of the leaves. In severe epidemics, similar symptoms could be observed on stems, sepals and petioles. Fruits are not affected (Jacob et al, 2008, Phytopathology, Vol. 99, No. 3, 270-281).

By "nematode", it is meant a roundworm of the Phylum Nematoda that colonizes a wide range of economically important host plants, such as tomatoes. Many different genera of nematode can punctually infect tomato plants but their incidence is generally low. The root-knot nematode, *Meloidogyne* spp., is by far the most widespread, damaging and economically important nematode infecting Tomato. Fives species of *Meloidogynes* are reported on tomato, i.e. *Meloidogyne incognita* (*M. incognita*, the most widespread), *Meloidogyne javanica* (*M. javanica*), *Meloidogyne arenaria* (*M. arenaria*), *Meloidogyne enterolobii* (*M. enterolobii*) and *Meloidogyne hapla* (*M. hapla*). Preferably, by nematode, it is meant *M. incognita* and/or *M. javanica*. The disease is characterized by the presence of galls or root-knots on infected plants. Symptoms of nematode infection include poor fruit yield, stunted growth, wilting, and susceptibility to other pathogens (Williamson, 1998, Annu. Rev. Phytopathol., 36:277-293).

By "tomato genome SL2.50", it is meant the tomato genome that has been published by Fernandez-Pozo et al., The Sol Genomics Network (SGN)—from genotype to phenotype to breeding. (2015) Nucleic Acids Res. Volume 43 (Database issue):D1036-41.

By "TY1 gene", it is meant the gene located on chromosome 6 that is known as conferring a resistance to TYLCV as described in Verlaan et al., 2013, PLOS Genetics, 9(3): e1003399. In other word, by TY1 gene, it is meant the resistant allelic version(s) of the gene that is/are able to confer resistance to TYLCV.

By "Mi-1 gene", it is meant the gene located on chromosome 6 that is known as conferring a resistance to nematodes as described in Seah et al., 2004, TAG, 108:1635-1642.

In other word, by Mi-1 gene, it is meant the resistant allelic version(s) of the gene that is/are able to confer resistance to nematodes.

By "OL4 gene", it is meant the gene located on chromosome 6 that is known as conferring a resistance to nematodes as described in Bai et al, 2005, TAG, 109(6): 1215-1223. In other word, by OL4 gene, it is meant the resistant allelic version(s) of the gene that is/are able to confer resistance to nematodes.

In the context of the present invention, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

In the context of the present invention, DNA strand and allele designation and orientation for the markers Mi2.3 and TO-0178067 is done according to the TOP/BOT method developed by Illumina (illumina.com/documents/products/technotes/technote_topbot.pdf).

DETAILED DESCRIPTION

According to a first aspect, the present invention is directed to a *Solanum lycopersicum* (*S. lycopersicum*) plant that is resistant to Tomato Yellow Leaf Curl Virus (TYLCV), powdery mildew (PM) and nematodes, wherein said plant comprises the (i) OL4 gene conferring resistance to PM and nematodes, and (ii) TY1 gene conferring resistance to TYLCV in coupling phase on chromosome 6, and wherein said plant does not comprise the Mi-1 gene conferring resistance to nematodes in said coupling phase on chromosome 6.

In some embodiments, said OL4 gene conferring resistance to PM and nematodes is identified by SSR-OL4 marker detection. In some embodiments, detection of the marker SSR-OL4 is performed by amplification, preferably by PCR, using a forward primer and a reverse primer which can be used to amplify the resistant/susceptible allele of marker SSR-OL4. In some embodiments, said amplification is followed by a digestion of the amplification products with restriction enzymes or by sequencing the amplification products. In particular, the forward primer and the reverse primer for detecting the marker SSR-OL4 may respectively comprise the sequences 5'-GAAATCGCAGAGTCACACTT-3' (SEQ ID NO: 1) and 5'-ATCCCGTGTAATTAATCGAA-3' (SEQ ID NO: 2). Using primers consisting of SEQ ID NO: 1 and SEQ ID NO: 2, detection of an amplification product of 382 bp indicates presence of the OL4 gene conferring resistance to PM and nematodes (see Table 1 below).

In some embodiments, said TY1 gene conferring resistance to TYLCV is identified by TO-0178067 and/or TY3-M3 markers detection. In some embodiments, detection of the TO-0178067 and/or TY3-M3 markers is performed by amplification, preferably by PCR, using specific primers which can be used to amplify the resistant/susceptible allele of each of the TO-0178067 and TY3-M3 markers.

In particular, detection of the TO-0178067 marker is performed using two forward primers, one being specific for the resistant allele and one being specific for the susceptible allele, and one common reverse primer. Said two forward primers may be selected so as to enable amplifying a nucleic acid comprising or consisting of SEQ ID NO: 3, or a fragment thereof including the [G/A] polymorphism at position 247 of SEQ ID NO: 3. For example, the forward primer for detecting the susceptible allele of the marker TO-0178067, by amplifying a nucleic acid consisting of sequence SEQ ID NO: 3, may consist of the sequence 5'-GAAGGTGACCAAGTT-CATGCTTTTGTTCCCCCAGCTGAGAGG-3' (SEQ ID NO: 4), the forward primer for detecting the resistant allele of the marker TO-0178067, by amplification of sequence SEQ ID NO: 3, may consists of the sequence 5'-GAAGGTCGGAGTCAACGGAT-TCTTTTGTTCCCCCAGCTGAGAGA-3' (SEQ ID NO: 5), and the common reverse primer may consists of the sequence 5'-GACCAACACGKCCTACGAGGTA-3' (SEQ ID NO: 6). Using primers consisting of sequences SEQ ID NO: 4, SEQ ID NO: 5 and SEQ ID NO: 6, detection of an adenine (A) rather than a guanine (G) at position 247 of the amplification product consisting of sequence SEQ ID NO: 3 indicates the presence of the TY1 gene conferring resistance to TYLCV (see Table 2 below).

In particular, the forward primer and the reverse primer for detecting the marker TY3-M3 may respectively consists of the sequences 5'-AGCTATCAGCTGCCAGAGACAT-3' (SEQ ID NO: 7) and 5'-CACCATCAT-TGTATCCAGAGAGC-3' (SEQ ID NO: 8). Using primers consisting of SEQ ID NO: 7 and SEQ ID NO: 8, detection of an amplification product of 220 bp indicates presence of the TY1 gene conferring resistance to TYLCV (see Table 1 below).

Alleles of the markers SSR-OL4 and TY3-M3 defined here above, conferring the resistance to Tomato Yellow Leaf Curl Virus (TYLCV), powdery mildew (PM) and nematodes, are as described in Table 1.

TABLE 1 alleles of the markers SSR-OL4 and TY3-M3 conferring the resistance to Tomato Yellow Leaf Curl Virus (TYLCV), powdery mildew (PM) and nematodes.

| Trait | Marker | Chromosome | Type | Resistance allele (bp) | Susceptible allele (bp) |
|---|---|---|---|---|---|
| PM and nematodes | SSR-OL4 | 6 | SSR | 382 | 389 |
| TYLCV | TY3-M3 | 6 | CAPS | 220 | 160 |

An allele (SEQ ID NO: 3 with A at position 247) of the marker TO-0178067 conferring the resistance to Tomato Yellow Leaf Curl Virus (TYLCV) defined here above is as described in Table 2.

TABLE 2

Marker TO-0178067 linked to Tomato Yellow Leaf Curl Virus (TYLCV) resistance, location on the tomato genome SL2.50 and flanking sequences. The SNP is identified in bold and in brackets. Chr.: Chromosome, R: Resistant, S: Susceptible, N is any of A, C, G or T, R is A or G, M is A or C, K is G or T, Y is T or C.

| Trait | Marker | Chr. | Position on chr. (SL2.50) | Type | Sequence surrounding the marker | R/S allele |
|---|---|---|---|---|---|---|
| TYLCV | TO-0178067 | 6 | SL2.50c h06_ 32660716 | SNP | CTACGCCACAGTTNAAANGTATGA ATATGATCTCCACAAYAAGGTTTC RTTAGAATGGCTGCTGGCTCTAGG TCCAAGCTTGGGTATTACTCGAGT CCCTGGCATYGGCCTYGTATTCAC TGATTTGACTTCTGGGATTCCAGC MAACTTCTCACGTTTTGTTACGAA YCTCCCTGCCTACCACCGGATACT TGTTTTCGTGTGTGTGAAATCSGT GCCTGTCCCTTTTGTTCCCCCAGC TGAGAG[G/A]TACCTCGTAGGMCG TGTTGGTCCTGCAGCTCATCGTTC CTATAGATGCATTGTCCGTTATGG TTACCGTGATGTTCAYCAGGATGT TGACTCCTTTGAATCCGAACTTGT CAGTAGGCTGGCTGATTTCATCCG GTATGATTGGTACAAGGCACATGG AATSATGGAGACATGCAACGAGGA TGACTGCTCACGTTCTGGTGCATC GTCAGGAGAATGTAGACTGACCG TTATAGGAACTCTAGATTTGTCAK GCGCACCAGCTTTTGAAGTCGAM GAAACCATGCAGCCTGCAAGCGT GTCTGTSGGKTTTCCTACAGTTGA AAGTGTAACRGATGTGATAGAGAT GCAAGCAGTGGAAAGAAGGGTGA GATTTGCGATAGATGACGAGTCG (SEQ ID NO: 3) | A/G |

In some embodiments, the presence or absence of Mi-1 gene conferring resistance to nematodes is identified by Mi2.3 marker detection. By marker Mi2.3, it is meant the single nucleotide polymorphism (SNP) as described below in Table 3.

TABLE 3

Marker Mi2.3 linked to nematode resistance, location on the tomato genome SL2.50 and flanking sequences. The SNP is identified in bold and in brackets Chr.: Chromosome, R: Resistant, S: Susceptible. N is any of A, C, G or T, R is A or G, S is G or C, K is G or T, Y is T or C, W is A or T.

| Trait | Marker | Chr. | Position on chr. (SL2.50) | Type | Sequence surrounding the marker | R/S allele |
|---|---|---|---|---|---|---|
| Nematodes | Mi2.3 | 6 | SL2.50c h06_ 2322335 | SNP | TGGCAGGTTCTTACAYCTTTTNAC TGTTCTAAAAAGATGTCTACAATTY GTTTSATCAAAGCCCCGACGGAAC TATTAAGTAGACGA[C/G]GTTAGTA AAATAACAAGCAACCAAAKCAGTT NNGAGAGATCACTTTTTTCCCANG GGATTTTTCTAGTAAGATTTTAAYC ARGCAWATTATCTWCTAAATATRT AGCGAGTTAGTATCATTATACTTT GTSTACAAATTAAATTTCGATTACT CTGGGTAAACAAGCCATATAGTAT GC (SEQ ID NO: 9) | G/C |

In some embodiments, the absence of the Mi-gene conferring resistance to nematodes may be identified by detecting the presence of "allele C" at position 88 of the amplification product consisting of sequence SEQ ID NO: 9. In some embodiments, detection of the presence or absence of Mi-1 gene conferring resistance to nematodes is performed by amplification, preferably by PCR, using specific primers selected so as to enable amplifying a nucleic acid comprising or consisting of SEQ ID NO: 9, or a fragment thereof including the [C/G] polymorphism at position 88 of SEQ ID NO: 9. In particular, detection of the marker Mi2.3 is performed using two forward primers, one being specific for the resistant allele and one being specific for the susceptible allele, and one common reverse primer. For example, the forward primer for detecting the resistant allele for the marker Mi2.3, by amplifying a nucleic acid consisting of sequence SEQ ID NO: 9, may consist of the sequence 5'-GAAGGTCGGAGTCAACGGATTCGACGGAACTAT-TAAGTAGACGAG-3' (SEQ ID NO: 10), the forward primer for detecting the susceptible allele for the marker Mi2.3, by amplifying a nucleic acid consisting of sequence SEQ ID NO: 9, may consist of the sequence 5'-GAAGGTGACCAAGTTCATGCTCGACGGAACTAT-TAAGTAGACGAC-3' (SEQ ID NO: 11), and the common reverse primer may consist of the sequence 5'-AACTGMTTTGGTTGCTTGTTATTTTACTAA-3' (SEQ ID NO: 12). Using the primers consisting of sequences SEQ ID NO: 10, SEQ ID NO: 11 and SEQ ID NO: 12, detection of a cytosine (C) rather than a guanine (G) at position 88 of the amplification product consisting of sequence SEQ ID NO: 9 indicates the absence of the Mi-1 gene conferring resistance to nematodes (see Table 3 above).

Where the Mi-1 gene conferring resistance to nematodes is present in trans in the plant, absence of the Mi-1 gene conferring resistance to nematodes in coupling phase on chromosome 6 with the OL4 gene conferring resistance to PM and nematodes, and TY1 gene conferring resistance to TYLCV, can be determined by an allelism test.

In some embodiments, the plant according to the invention comprises the here above described specific alleles conferring the resistances to Tomato Yellow Leaf Curl Virus (TYLCV), powdery mildew (PM) and nematodes at heterozygous or homozygous state.

In some embodiments, when the plant according to the invention comprises the here above described specific alleles conferring the resistances to Tomato Yellow Leaf Curl Virus (TYLCV), powdery mildew (PM) and nematodes at heterozygous state, said plant further comprises the Mi-1 gene conferring resistance to nematodes in trans on chromosome 6. By "Mi-1 gene conferring resistance to nematodes in trans on chromosome 6", it is meant that the Mi-1 gene conferring resistance to nematodes is not on the same coupling phase as the resistance OL4 and TY1 genes, i.e. that the Mi-1 gene conferring resistance to nematodes is not on the same chromosome as the resistance OL4 and TY1 genes. In other word, it means that the plant according to the invention may comprise the resistance OL4 and TY1 genes in coupling phase on the first homologous chromosome 6, without having the Mi-1 gene conferring resistance to nematodes in said coupling phase, but having the Mi-1 gene conferring resistance to nematodes in trans on the second homologous chromosome 6.

Accordingly, insofar as the OL4 gene conferring resistance to PM and nematodes, and TY1 gene conferring resistance to TYLCV can be identified by the specific alleles described in Tables 1 and 2, a plant of the invention comprises one of the following combinations of alleles:

Combination 1:
(i) an allele of 220 bp of the marker TY3-M3 and/or an "allele A" of the TO-0178067 marker, an allele of 382 bp of the marker SSR-OL4, and an "allele C" of the marker Mi2.3 physically located on the first homologous chromosome 6, and
(ii) an allele of 160 bp of the marker TY3-M3 and/or an "allele G" of the TO-0178067 marker, an allele of 389 bp of the marker SSR-OL4, and an "allele G" of the marker Mi2.3 physically located on the second homologous chromosome 6; or Combination 2:
(i) an allele of 220 bp of the marker TY3-M3 and/or an "allele A" of the TO-0178067 marker, an allele of 382 bp of the marker SSR-OL4, and an "allele C" of the marker Mi2.3 physically located on the first homologous chromosome 6, and
(ii) an allele of 160 bp of the marker TY3-M3 and/or an "allele G" of the TO-0178067 marker, an allele of 389 bp of the marker SSR-OL4, and an "allele C" of the marker Mi2.3 physically located on the second homologous chromosome 6; or Combination 3:
(i) an allele of 220 bp of the marker TY3-M3 and/or an "allele A" of the TO-0178067 marker, an allele of 382 bp of the marker SSR-OL4, and an "allele C" of the marker Mi2.3 physically located on the first homologous chromosome 6, and
(ii) an allele of 220 bp of the marker TY3-M3 and/or an "allele A" of the TO-0178067 marker, an allele of 382 bp of the marker SSR-OL4, and an "allele C" of the marker Mi2.3 physically located on the second homologous chromosome 6.

In some embodiments, said OL4 gene conferring resistance to PM and nematodes, and TY1 gene conferring resistance to TYLCV are chosen from those present in the genome of the plant TCR1, which seeds are deposited under the NCIMB accession number 42490.

In some embodiments, said OL4 gene conferring resistance to PM and nematodes, and TY1 gene conferring resistance to TYLCV are as found in the genome of the plant TCR1, which seeds are deposited under the NCIMB accession number 42490.

In some embodiments, the *S. lycopersicum* plant according to the invention is the plant TCR1, which seeds are deposited under NCIMB accession number 42490.

In some embodiments, the *S. lycopersicum* plant according to the invention is a parthenocarpic plant.

In some embodiments, a plant according to the invention may be a progeny or offspring of a plant grown from the deposited seeds of *S. lycopersicum* plant TCR1, deposited at the NCIMB under the accession number 42490. Plants grown from the deposited seeds are heterozygously resistant to TYLCV, PM and nematodes; they thus bear in their genome the OL4 gene conferring resistance to PM and nematodes and the TY1 gene conferring resistance to TYLCV in coupling phase on chromosome 6 as defined here above at heterozygous state, but do not bear the Mi-1 gene conferring resistance to nematodes in said coupling phase on chromosome 6. They can be used to transfer this combination of genes in another background by crossing and selfing and/or backcrossing. A progeny of a plant obtained from the deposited seed can be identified by one skilled in the art, for example by using the markers SSR-OL4, TO-0178067, TY3-M3 and Mi2.3.

The resistance to TYLCV, PM and nematodes is advantageously determined by comparison to a susceptible (commercial) variety, for example the DESIDERIO, TAMARIS, FLORENZIA, PIETRO, LIPSO, VOLUPTUOSO, TRINIDAD, or DUNCAN varieties.

Resistance to TYLCV is preferably determined on the basis of the pathological test described in the paragraph "TYLCV test" of the examples, i.e. by determining the yellowing and curling of the leaves. Preferably, this criterion is determined a few weeks after inoculation, preferably between at 3 or 4 weeks after inoculation. A resistance scoring is used to evaluate the resistance of the tested plant. Preferably, the resistance scoring for evaluation the resistance to TYLCV is a scoring system ranging from 9 (the most resistant level or the least symptomatic level) to 1 (the least resistance level or the most symptomatic level). More precisely, the score of 9 indicates that there is no symptoms on the leaves; the score of 8 indicates slight symptoms in a close inspection with slight veins discoloration on edge of apical leaves; the score of 6 indicates slight symptoms on apical part of the plant and minor curling; the score of 5 indicates moderate yellowing, curling and cupping on apical leaves with a plant growth that continues normally; the score of 3 indicates strong symptoms with yellowing, curling and cupping with moderate dwarfism; and the score of 1 indicates very strong symptoms on apical part with yellowing, curling and cupping with severe dwarfism, and leaflet with string size reduction and non-developed. In such a scoring system, a plant population is resistant if it has about 50%, about 55%, about 60%, about 65%, about 70%, about 75%, about 80%, about 85%, about 90%, about 95%, or about 100% of the plants in the least symptomatic levels of 9 or 8. In one embodiment, a plant population is resistant to the virus if it has greater than 60% of the plants in the least symptomatic levels of 9 or 8. In one embodiment, a plant population is obviously resistant to the virus if it has greater than 70% of the plants in the least symptomatic levels of 9 or 8. In one embodiment, a plant population is highly resistant to the virus if it has greater than 80% of the plants in the least symptomatic levels of 9 or 8. In one embodiment, a plant population is extremely resistant to the virus if it has greater than 90% of the plants in the least symptomatic levels of 9 or 8. A plant population is susceptible if it has about 50%, about 55%, about 60%, about 65%, about 70%, about 75%, about 80%, about 85%, about 90%, about 95%, or about 100% of the plants in the most symptomatic levels of 1 or 3. In one embodiment, a plant population is susceptible to the virus if it has greater than 60% of the plants in the most symptomatic levels of 1 or 3. In one embodiment, a plant population is obviously susceptible to the virus if it has greater than 70% of the plants in the most symptomatic levels of 1 or 3. In one embodiment, a plant population is highly susceptible to the virus if it has greater than 80% of the plants in the most symptomatic levels of 1 or 3. In one embodiment, a plant population is extremely susceptible to the virus if it has greater than 90% of the plants in the most symptomatic levels of 1 or 3.

Resistance to PM is preferably determined on the basis of the pathological test described in the paragraph "*Oidium* test" of the examples, i.e. by evaluating the percentage of leaves area with sporulation of the fungus. Preferably, this criterion is determined a few days after inoculation, preferably between 8 to 30 days, still preferably 10 to 20 days after inoculation. A resistance scoring is used to evaluate the resistance of the tested plant. Preferably, the resistance scoring for evaluation the resistance to PM is a scoring system ranging from 9 (the most resistant level or the least symptomatic level) to 1 (the least resistance level or the most symptomatic level). More precisely, the score of 9 indicates that there is no sporulation on the leave area; the score of 8 indicates a slight sporulation with 1% to 5% of leave area infected; the score of 7 indicates a moderate sporulation with leave area infected between 6% and 25%; the score of 5 indicates a moderate sporulation with leave area infected between 26% and 50%; the score of 3 indicates a strong sporulation with leave area infected between 51% and 75%; and the score of 1 indicates a very strong sporulation with more than 75% of leave area infected. In such a scoring system, a plant population is resistant if it has about 50%, about 55%, about 60%, about 65%, about 70%, about 75%, about 80%, about 85%, about 90%, about 95%, or about 100% of the plants in the least symptomatic levels of 9 or 8. In one embodiment, a plant population is resistant to PM if it has greater than 60% of the plants in the least symptomatic levels of 9 or 8. In one embodiment, a plant population is obviously resistant to PM if it has greater than 70% of the plants in the least symptomatic levels of 9 or 8. In one embodiment, a plant population is highly resistant to PM if it has greater than 80% of the plants in the least symptomatic levels of 9 or 8. In one embodiment, a plant population is extremely resistant to PM if it has greater than 90% of the plants in the least symptomatic levels of 9 or 8. A plant population is susceptible if it has about 50%, about 55%, about 60%, about 65%, about 70%, about 75%, about 80%, about 85%, about 90%, about 95%, or about 100% of the plants in the most symptomatic levels of 3 or 1. In one embodiment, a plant population is susceptible to PM if it has greater than 60% of the plants in the most symptomatic levels of 3 or 1. In one embodiment, a plant population is obviously susceptible to PM if it has greater than 70% of the plants in the most symptomatic levels of 3 or 1. In one embodiment, a plant population is highly susceptible to PM if it has greater than 80% of the plants in the most symptomatic levels of 3 or 1. In one embodiment, a plant population is extremely susceptible to PM if it has greater than 90% of the plants in the most symptomatic levels of 3 or 1.

Resistance to nematodes is preferably determined on the basis of the pathological test described in the paragraph "Nematode test" of the examples, i.e. by evaluating the numbers of galls present on the whole root system of each tested plant. Preferably, this criterion is determined a few weeks after inoculation, preferably between four to eight weeks, still preferably four weeks after inoculation. The resistance test is for example determined at four weeks after inoculation, and a resistance scoring is used to evaluate the resistance of the tested plant. Preferably, the resistance scoring for evaluation the resistance to nematodes is a scoring system ranging from 9 (the most resistant level or the least symptomatic level) to 1 (the least resistance level or the most symptomatic level). More precisely, the score of 9 indicates that the root system of the plant has no galls; the score of 7 indicates that the root system of the plant has between 1% and 30% of galls with limited size; the score of 5 indicates that the root system of the plant has more than 30% of galls, the score of 3 indicates that the root system of the plant has at least 60% of galls, and the score of 1 indicates that the root system of the plant has at least 90% of galls. In some embodiments, a plant population is considered as (i) resistant if all the plants are in class 9, (ii) intermediate resistant if all the plants are in class 7 and/or 5, and (iii) susceptible if all the plants are in class 3 and/or 1. In some embodiments, a plant population is resistant if it has about 50%, about 55%, about 60%, about 65%, about 70%, about 75%, about 80%, about 85%, about 90%, about 95%, or about 100% of the plants in the least symptomatic levels of 9. In some embodiments, a plant population is resistant to nematode if it has greater than 60% of the plants in the least symptomatic levels of 9. In some embodiments, a plant population is obviously resistant to nematodes if it has greater than 70% of the plants in the least symptomatic levels of 9. In one embodiment, a plant population is highly resistant to nematodes if it has greater than 80% of the plants in the least symptomatic levels of 9. In some embodiments, a plant population is extremely resistant to nematodes if it has greater than 90% of the plants in the least symptomatic levels of 9. In some embodiments, a plant population is intermediate resistant if it has about 50%, about 55%, about 60%, about 65%, about 70%, about 75%, about 80%, about 85%, about 90%, about 95%, or about 100% of the plants in the most symptomatic levels of 7 or 5. In some embodiments, a plant population is intermediate resistant to nematodes if it has greater than 60% of the plants in the most symptomatic levels of 7 or 5. In some embodiments, a plant population is obviously intermediate resistant to nematodes if it has greater than 70% of the plants in the most symptomatic levels of 7 or 5. In some embodiments, a plant population is susceptible if it has about 50%, about 55%, about 60%, about 65%, about 70%, about 75%, about 80%, about 85%, about 90%, about 95%, or about 100% of the plants in the most symptomatic levels of 3 or 1. In some embodiments, a plant population is susceptible to nematodes if it has greater than 60% of the plants in the most symptomatic levels of 3 or 1. In some embodiments, a plant population is obviously susceptible to nematodes if it has greater than 70% of the plants in the most symptomatic levels of 3 or 1. In some embodiments, a plant population is highly susceptible to nematodes if it has greater than 80% of the plants in the most symptomatic levels of 3 or 1. In some embodiments, a plant population is extremely susceptible to nematodes if it has greater than 90% of the plants in the most symptomatic levels of 3 or 1.

Therefore, a plant according to the invention preferably displays a score of 9 in the pathological test for TYLCV resistance, a score of 9 or 8 for the pathological test for *Oidium* resistance, and a score of 9 or 7 for the pathological test for nematodes resistance.

In some embodiments, the plant according to the invention, i.e. a plant carrying the resistance OL4 and TY1 genes in cis on chromosome 6, can be identified using an allelism test. To perform an allelism test, material that is homozygous for a known determinant, e.g. a plant that comprises the resistance OL4 and TY1 genes in cis on chromosome 6 in homozygous state but that does not comprise the Mi-1 gene conferring resistance to nematodes in cis with said resistance OL4 and TY1 genes, so-called a "tester plant", is crossed with material that comprises the alleles to be tested at homozygous state, i.e. the "donor plant". For example, said tester plant is derived from the TCR1 plant, which seeds have been deposited under the NCIMB number 42490. The donor plant to be tested should be or should be made homozygous for the alleles to be tested. The one skilled in the art knows how to obtain a plant that is homozygous for the allele to be tested. When, in the F2 of the cross between the donor plant and the tester plant, no segregation for the alleles is observed, the resistance alleles of the donor plant and the tester plant are considered as equivalent or the same. In the frame of the present invention, when in the F2 of the cross between a plant carrying the resistance OL4 and TY1 genes in cis on chromosome 6 in homozygous state and not carrying the Mi-1 gene conferring resistance to nematodes in cis with said resistance OL4 and TY1 genes with a plant to be tested, no segregation of the resistant alleles for markers SSR-OL4, TO-0178067, TY3-M3 and of susceptible allele for the marker Mi2.3 is observed, it means that the tested plant carried the resistance OL4 and TY1 genes in cis on chromosome 6 without carrying the Mi-1 gene conferring resistance to nematodes in cis with said resistance OL4 and TY1 genes.

It is noted that the seeds or plants of the invention may be obtained by different processes, in particular technical processes such as UV mutagenesis or genetic engineering such as guided recombination, and are not exclusively obtained by means of an essentially biological process.

According to such an aspect, the invention relates to a tomato plant or seed, preferably a non-naturally occurring tomato plant or seed, which may comprise one or more mutations in its genome, which provides the mutant plant a resistance to TYLCV, PM and nematodes, which mutation is as present, for example, in the genome of plants of which a representative sample was deposited with the NCIMB under deposit number NCIMB 42490.

Preferably, the mutations are the integration of the OL4 gene and TY1 gene as described above, in replacement of the homologous sequences of a *S. lycopersicum* plants. Even more preferably, the mutation is the substitution of the sequence comprising SSR-OL4, TO-0178067 and/or TY3-M3 markers on chromosome 6 of *S. lycopersicum* genome, or a fragment thereof, by the homologous sequence on chromosome 6 present in the genome of a plant of which a representative sample was deposited with the NCIMB under deposit number NCIMB 42490, wherein the sequence or fragment thereof confers resistance to TYLCV, PM and nematodes. Such mutation may further include the deletion or the inactivation of the Mi-1 gene as described above.

In an embodiment, the invention relates to a method for obtaining a tomato plant or seed carrying one or more mutations in its genome, which provides the plant with a resistance to TYLCV, PM and nematodes. Such a method is illustrated in example 3 and may comprise:

a) treating M0 seeds of a tomato plant to be modified with a mutagenic agent to obtain M1 seeds;

b) growing plants from the thus obtained M1 seeds to obtain M1 plants;

c) producing M2 seeds by self-fertilisation of M1 plants; and d) optionally repeating step b) and c) n times to obtain M2+n seeds.

The M2+n seeds are grown into plants and submitted to TYLCV, PM and nematodes infection. The surviving plants, or those with the milder symptoms of TYLCV, PM and nematodes infection, are multiplied one or more further generations while continuing to be selected for their resistance to TYLCV, PM and nematodes.

In this method, the M1 seeds of step a) can be obtained via chemical mutagenesis such as EMS mutagenesis. Other chemical mutagenic agents include but are not limited to, diethyl sulfate (des), ethyleneimine (ei), propane sultone, N-methyl-N-nitrosourethane (mnu), N-nitroso-N-methyl-urea (NMU), N-ethyl-N-nitrosourea(enu), and sodium azide.

Alternatively, the mutations are induced by means of irradiation, which is for example selected from x-rays, fast neutrons, UV radiation.

In another embodiment of the invention, the mutations are induced by means of genetic engineering. Such mutations also include the integration of sequences conferring the TYLCV, PM and nematodes resistance, as well as the substitution of residing sequences by alternative sequences conferring the TYLCV, PM and nematodes resistance.

The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated thru the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM), Cisgenesis and intragenesis, RNA-dependent DNA methylation (RdDM, which does not necessarily change nucleotide sequence but can change the biological activity of the sequence), Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease re-engineered homing endonucleases, DNA guided genome editing (Gao et al., Nature Biotechnology (2016), doi: 10.1038/nbt.3547, incorporated by reference in its entirety), and Synthetic genomics). A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

According to a second aspect, the present invention is directed to parts of a plant according to the invention.

In some embodiments, a part of a plant is a plant cell. The invention thus provides a cell, preferably an isolated cell, of a S. lycopersicum plant according to the invention, i.e. a cell that comprises the (i) OL4 gene conferring resistance to PM and nematodes and (ii) TY1 gene conferring resistance to TYLCV in coupling phase on chromosome 6, and that does not comprises the Mi-1 gene conferring resistance to nematodes in said coupling phase on chromosome 6.

In some embodiments, said OL4 gene conferring resistance to PM and nematodes, and TY1 gene conferring resistance to TYLCV in coupling phase on chromosome 6 are as defined in the first aspect of the invention.

In some embodiments, the alleles conferring the resistances to Tomato Yellow Leaf Curl Virus (TYLCV), powdery mildew (PM) and nematodes are as described in Tables 1 and 2.

In some embodiments, the plant part according to the invention thus comprises the combinations of alleles 1, 2 or 3 as described in the first aspect of the invention.

In some embodiments, the combination of genes or alleles as described here above is preferably chosen from those present in the genome of a plant corresponding to the deposited material TCR1 (NCIMB accession number 42490).

In some embodiments, the combination of genes or alleles as described here above is preferably as found in the genome of a plant corresponding to the deposited material TCR1 (NCIMB accession number 42490).

A plant cell of the invention may have the capacity to be regenerated into a whole plant, said plant having a commercially acceptable fruit quality.

Alternatively, the invention is also directed to plant cells which are not regenerable, and thus are not capable of giving rise to a whole plant.

According to another embodiment, the plant part is any other part of a plant according to the invention; it may be in particular seeds, reproductive material, roots, flowers, fruits, in particular parthenocarpic fruits, rootstock or scion. Such a part comprises a cell as defined above.

The present invention is also directed to a tissue culture of regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and thus comprises the (i) OL4 gene conferring resistance to PM and nematodes, and (ii) TY1 gene conferring resistance to TYLCV, in coupling phase on chromosome 6, and does not comprises the Mi-1 gene conferring resistance to nematodes in said coupling phase on chromosome 6.

The tissue culture will preferably be capable of regenerating plants having the physiological and morphological characteristics of the foregoing tomato plant, and of regenerating plants having substantially the same genotype as the foregoing tomato plant.

The present invention also provides tomato plants regenerated from the tissue cultures of the invention.

The invention also provides a protoplast of the plant defined above, or from the tissue culture defined above, said protoplast comprising the (i) OL4 gene conferring resistance to PM and nematodes, and (ii) TY1 gene conferring resistance to TYLCV, in coupling phase on chromosome 6, and does not comprises the Mi-1 gene conferring resistance to nematodes in said coupling phase on chromosome 6.

All the embodiments detailed in the preceding section in connection with the first aspect of the invention are also preferred embodiments according to this second aspect of the invention.

The invention is more particularly concerned with seed of a S. lycopersicum plant, giving rise when grown up to S. lycopersicum plant resistant to TYLCV, PM and nematodes as defined above. Such seed are thus 'seed of a plant of the invention', i.e. seed giving rise to a plant of the invention. The invention is also concerned with seed from a plant of the invention, i.e. obtained from such a plant after selfing or crossing, provided however that the plant obtained from said seed is resistant to TYLCV, PM and nematodes due to the combination of OL4 and TY1 genes in cis as defined here above conferring said resistance trait, and the absence of Mi-1 gene conferring resistance to nematodes in cis with said OL4 and TY1 genes.

According to a third aspect, the present invention is also directed to the use of a *S. lycopersicum* plant as detailed according to the first aspect of the invention, i.e. resistant to TYLCV, PM and nematodes, as a breeding partner in a breeding program for obtaining *S. lycopersicum* plants resistant to TYLCV, PM and nematodes. Indeed, such a *S. lycopersicum* plant according to the first aspect harbors in its genome the combination in cis on chromosome 6 of OL4 and TY1 genes as defined here above conferring said resistances PM, nematodes and TYLCV, but does not comprises the Mi-1 gene conferring resistance to nematodes in cis with said OL4 and TY1 genes. By crossing this plant with susceptible or less resistant plants, it is thus possible to transfer these genes, conferring the desired phenotype to the progeny. A plant according to the invention can thus be used as a breeding partner for introgressing in cis the resistance OL4 and TY1 genes conferring the desired phenotype into a *S. lycopersicum* plant or germplasm, without introgressing the Mi-1 gene conferring resistance to nematodes in cis with said resistance OL4 and TY1 genes. The invention is also directed to the same use with plants and/or seed of plant TCR1 as deposited at NCIMB under accession number 42490. Said plants are also suitable as introgression partners in a breeding program aiming at conferring the desired phenotype to a *S. lycopersicum* plant or germplasm.

In such a breeding program, the selection of the progeny displaying the desired phenotype, or bearing sequences linked to the desired phenotype, can advantageously be carried out on the basis of the allele of the markers disclosed here above. The progeny is preferably selected on the presence of one or more of the following specific alleles: an allele of 382 bp of the marker SSR-OL4, an allele A of the marker TO-0178067 on chromosome 6, an allele of 220 bp of the marker TY3-M3, and an allele C of the marker Mi2.3. The selection can alternatively be made on the basis of the alleles of all the markers. The selection is preferably made on the basis of the combination of alleles 1, 2 or 3 as described in the first aspect of the invention.

The selection of the progeny having the desired phenotype can also be made on conditions of pathogens infestation, as disclosed inter alia in the section TYLCV test, PM test and/or nematodes test of the examples.

The selection of progeny having the desired phenotype can also be made using an allelism test as described here above.

A plant according to the invention, or as deposited under accession number NCIMB 42490, is thus particularly valuable in a marker assisted selection program for obtaining commercial *S. lycopersicum* lines and varieties resistant to TYLCV, PM and nematodes.

Any embodiment described for the $1^{st}$ and $2^{nd}$ aspects of the invention is also applicable to this aspect of the invention.

According to a fourth aspect, the invention also concerns methods for the production of *S. lycopersicum* plants resistant to TYLCV, PM and nematodes, especially commercial plants.

A method or process for the production of a plant having these features comprises the following steps:
a) Crossing a plant according to the first aspect of the invention (e.g. a plant grown from the deposited seeds (NCIMB 42490), or a progeny thereof bearing the combination in cis of the OL4 gene conferring resistance to PM and nematodes and the TY1 gene conferring resistance to TYLCV, but not bearing the Mi-1 gene conferring resistance to nematodes in cis with said OL4 and TY1 genes) and a susceptible or less resistant *S. lycopersicum* plant, in which the desired phenotype is to be imported or improved,
b) Selecting one plant resistant to TYLCV, PM and nematodes in the progeny thus obtained, or one plant bearing the combination in cis of the OL4 gene conferring resistance to PM and nematodes and the TY1 gene conferring resistance to TYLCV, but not bearing the Mi-1 gene conferring resistance to nematodes in cis with said OL4 and TY1 genes,
c) Optionally self-pollinating one or several times the resistant plant obtained at step b) and selecting a plant resistant TYLCV, PM and nematodes in the progeny thus obtained,
d) Backcrossing the resistant plant selected in step b) or c) with a susceptible *S. lycopersicum* plant (i.e. susceptible to TYLCV, PM and nematodes), and
e) Selecting a plant resistant to TYLCV, PM and nematodes.

Alternatively, the method or process may comprise the following steps:
a1) Crossing a plant according to the first aspect of the invention (e.g. a plant grown from the deposited seeds (NCIMB 42490), or a progeny thereof bearing the combination in cis of the OL4 gene conferring resistance to PM and nematodes and the TY1 gene conferring resistance to TYLCV, but not bearing the Mi-1 gene conferring resistance to nematodes in cis with said OL4 and TY1 genes) and a susceptible or less resistant *S. lycopersicum* plant, in which the desired phenotype is to be imported or improved, thus generating the F1 population,
a2) Increasing the F1 hybrid to create F2 population,
b) Selecting resistant individuals in the progeny thus obtained,
c) Optionally self-pollinating one or several times the resistant plant obtained at step b) and selecting a resistant plant in the progeny thus obtained,
d) Backcrossing the resistant plant selected in step a2), c) or d) with a susceptible *S. lycopersicum* plant (i.e. susceptible to TYLCV, PM and nematodes),
e) Selecting a plant resistant to TYLCV, PM and nematodes.

In some embodiments, it can be selected at steps a2), b), c) and e) plant resistant to TYLCV, PM and nematodes.

The plant selected at step e) is preferably a commercial plant, especially a plant having fruits which weigh at least 25 g, or at least 50 g at full maturity in normal culture conditions.

The one skilled in the art is able to define a commercial plant depending on the market.

Preferably, steps d) and e) are repeated at least twice and preferably three times, not necessarily with the same susceptible *S. lycopersicum* plant. Said susceptible *S. lycopersicum* plant is preferably a breeding line.

The self-pollination and backcrossing steps may be carried out in any order and can be intercalated, for example a backcross can be carried out before and after one or several self-pollinations, and self-pollinations can be envisaged before and after one or several backcrosses.

In some embodiments, such a method is advantageously carried out by using markers as described in the first aspect of the invention for one or more of the selections carried out at steps b), c) and/or e) for selecting plants resistant to TYLCV, PM and nematodes. The markers are preferably at least one or more of the markers SSR-L4, TO-0178067, TY3-M3 as described in the first aspect of the invention, and the marker Mi2.3 as described in the first aspect of the invention, or of all the markers SSR-L4, TO-0178067, TY3-M3, and Mi23 as described in the first aspect of the invention. According to a preferred embodiment, the selection is made on the basis of the alleles of the markers SSR-L4, TO-0178067, TY3-M3, and Mi2.3 as described in the first aspect of the invention.

The plant selected at any one of steps b), c) and/or e) is preferably selected on the presence of one or more of the following alleles: an allele of 382 bp of the marker SSR-OL4, an allele A of the marker TO-0178067, an allele of 220 bp of the marker TY3-M3, and an allele C of the marker Mi2.3. Still preferably, plant selected at any one of steps b), c) and/or e) is preferably selected on the presence of the combination of alleles 1, 2 or 3 as described in the first aspect of the invention.

The selection of the progeny having the desired phenotype can also be made on conditions of pathogen infestation, as disclosed inter alia the section TYLCV test, PM test and/or nematodes test of the examples.

The method used for allele detection can be based on any technique allowing the distinction between two different alleles of a marker, on a specific chromosome.

The present invention also concerns a plant obtained or obtainable by such a method.

Such a plant is indeed a *S. lycopersicum* plant that is resistant to TYLCV, PM and nematodes, according to the first aspect of the invention.

The invention is also directed to a method for obtaining commercial *S. lycopersicum* plants that are resistant to TYLCV, PM and nematodes, said method comprising the steps of:
Backcrossing a plant obtained by germinating the deposited seeds TCR1 (NCIMB accession number 42490) or a progeny thereof bearing the combination in cis of the OL4 gene conferring resistance to PM and nematodes and the TY1 gene conferring resistance to TYLCV, but not bearing the Mi-1 gene conferring resistance to nematodes in cis with said OL4 and TY1 genes, with a *S. lycopersicum* plant, for example a *S. lycopersicum* plant susceptible to TYLCV, PM and nematodes,
Selecting a plant resistant TYLCV, PM and nematodes.

The selection in the second step is preferably carried out as detailed above for the other methods of the invention. Said selection is preferably carried out on the presence of one or more of the specific alleles of the markers SSR-L4, TO-0178067, TY3-M3 and Mi2.3 as described here above, such as for example on the presence of the combination of alleles 1, 2 or 3 as described in the first aspect of the invention, or the combination of alleles as found in plant TCR1. Said selection can be carried out using an allelism test as described here above. In some embodiments, said selection is carried out using an allelism test as described here above combined with the detection of the presence of one or more of the specific alleles of the markers SSR-OL4, TO-0178067, TY3-M3 and Mi2.3 as described here above, such as for example on the presence of the combination of alleles 1, 2 or 3 as described in the first aspect of the invention, or the combination of alleles as found in plant TCR1.

The plant selected is preferably a commercial plant, especially a plant having fruits which weigh at least 25 g, or at least 50 g at full maturity in normal culture conditions. The one skilled in the art is able to define a commercial plant depending on the market.

Also provided are methods for producing *S. lycopersicum* plants seed. In some embodiments, the methods comprise crossing the *S. lycopersicum* plant according to the invention with itself or with another *S. lycopersicum* plant, and harvesting the resultant seed.

The present invention also provides methods for detecting and/or selecting a *S. lycopersicum* plant that is resistant to TYLCV, powdery mildew and nematodes, wherein said method comprises:
a) detecting the presence or absence of:
OL4 gene conferring resistance to PM and nematodes, said OL4 gene being identified by SSR-OL4 marker detection,
TY1 gene conferring resistance to TYLCV, said TY1 gene being identified by TO-0178067 and/or TY3-M3 marker detection, and
Mi-1 gene conferring resistance to nematodes, said Mi-1 gene being identified by Mi2.3 marker detection; and
b) selecting as a plant resistant to TYLCV, PM and nematodes the *S. lycopersicum* plant in which the resistance OL4 and TY1 genes have been detected as present in coupling phase on chromosome 6 and the Mi-1 gene conferring resistance to nematodes has been detected as absent in said coupling phase.

In some embodiments, said method comprises the steps consisting of:
a) crossing the plant to be tested that comprises the alleles of resistance to be tested at homozygous state with a plant that comprises the resistance OL4 and TY1 genes in cis on chromosome 6 in homozygous state but that does not comprise the Mi-1 gene conferring resistance to nematodes in cis with said OL4 and TY1 genes,
b) detecting the markers SSR-OL4, TO-0178067, TY3-M3, and Mi2.3, in the F2 plants obtained from said cross,
wherein, in the F2 plants obtained from said cross, no segregation of the resistant alleles of markers SSR-OL4, TO-0178067, TY3-M3 and of susceptible allele of the marker Mi2.3 is observed, indicates that the plant to be tested carried the resistance OL4 and TY1 genes in cis on chromosome 6 without carrying the Mi-1 gene conferring resistance to nematodes in cis with said OL4 and TY1 genes. In some embodiments, said plant at step a) that comprises the resistance OL4 and TY1 genes in cis on chromosome 6 in homozygous state but that does not comprise the Mi-1 gene conferring resistance to nematodes in cis with said OL4 and TY1 genes is derived from the TCR1 plant, which seeds have been deposited under the NCIMB number 42490.

In some embodiments, detection of the marker SSR-OL4 is performed by PCR using a forward primer and a reverse primer which can be used to amplify the resistant/susceptible allele of marker SSR-OL4. In some embodiments, said PCR is followed by a digestion of the amplification products with restriction enzymes or by sequencing the amplification products.

In particular, the forward primer and the reverse primer for detecting the marker SSR-OL4 may respectively consist of the sequences 5'-GAAATCGCAGAGTCACACTT-3' (SEQ ID NO: 1) and 5'-ATCCCGTGTAATTAATCGAA-3' (SEQ ID NO: 2).

In a preferred embodiment, the PCR comprises an initial denaturation step followed by cycles of denaturation-annealing-elongation steps, and a final elongation step. In some embodiments, cycles of denaturation-annealing-elongation steps are performed in two rounds.

The initial denaturation step may be performed under heating conditions ranging from 90° C. to 105° C., during 15 s to 15 min. Preferably, the heating conditions range from 92° C. to 102° C., more preferably from 95° C. to 100° C., still more preferably the heating conditions are at 95° C. Preferably, the initial denaturation step is performed during 1 min to 15 min, more preferably during 8 min to 12 min, still more preferably during 5 min to 10 min, and still more preferably the initial denaturation step is performed during 5 min. In a preferred embodiment, the initial denaturation step is performed at 95° C. during 5 min.

Each cycle of denaturation-annealing-elongation step includes a denaturation phase under heating conditions, followed by an annealing phase performed under conditions which allow the hybridization of the primers and the probe to the sequence to be amplified, and an elongation phase performed under conditions which allow the polymerase to synthesize an extension product from each primer that is annealed to the sequence to be amplified.

On the first round, the denaturation phase may be performed between 90° C. to 105° C., preferably 92° C. to 100° C., during 10 s to 4 min, preferably during 10 s to 2 min, more preferably during 15 s to 1 min.

The annealing phase may be performed between 35° C. and 70° C., preferably between 40° C. to 65° C., more preferably between 45° C. to 60° C., still more preferably between 50° C. to 60° C., during 5 s to 2 min, preferably during 10 s to 1.5 min, more preferably during 15 s to 50 S.

The elongation phase may be performed between 40° C. and 80° C., preferably between 50° C. to 75° C., more preferably between 60° C. to 72° C., during 10 s to 5 min, preferably during 20 s to 3 min, more preferably during 30 s to 1 min.

In a preferred embodiment, on the first round the denaturation phase is performed at 95° C. during 15 s, the annealing phase is performed at 57° C. during 15 s and the elongation phase is performed at 72° C. during 30 s. The denaturation-annealing-elongation step may be repeated during 5 to 30 cycles, preferably during 10 to 20 cycles. Still more preferably, the denaturation-annealing-elongation step is repeated during 10 cycles.

On the second round, the denaturation phase may be performed between 90° C. to 105° C., preferably 92° C. to 100° C., during 10 s to 4 min, preferably during 10 s to 2 min, more preferably during 15 s to 1 min.

The annealing phase may be performed between 35° C. and 70° C., preferably between 40° C. to 65° C., more preferably between 45° C. to 60° C., still more preferably between 50° C. to 60° C., during 5 s to 2 min, preferably during 10 s to 1.5 min, more preferably during 15 s to 50 S.

The elongation phase may be performed between 40° C. and 80° C., preferably between 50° C. to 75° C., more preferably between 60° C. to 72° C., during 10 s to 5 min, preferably during 20 s to 3 min, more preferably during 30 s to 1 min.

In a preferred embodiment, the second round the denaturation phase is performed at 95° C. during 15 s, the annealing phase is performed at 52° C. during 15 s and the elongation phase is performed at 72° C. during 30 s. The denaturation-annealing-elongation step may be repeated during 10 to 40 cycles, preferably during 15 to 30 cycles. Still more preferably, the denaturation-annealing-elongation step is repeated during 25 cycles.

The final elongation step may be performed under heating conditions ranging from 60° C. to 90° C., during 15 s to 15 min. Preferably, the heating conditions range from 65° C. to 80° C., more preferably from 70° C. to 80° C. Preferably, the final elongation step is performed during 1 min to 15 min, more preferably during 8 min to 12 min, still more preferably during 5 min to 10 min. In a preferred embodiment, the final elongation step is performed at 72° C. during 10 min.

In some embodiments, detection of the TY3-M3 marker is performed by PCR using a forward primer and a reverse primer which can be used to amplify the resistant/susceptible allele of marker TY3-M3. In some embodiments, said PCR is followed by a digestion of the amplification products with restriction enzymes (e.g. Mse1) or by sequencing the amplification products. In particular, the forward primer and the reverse primer for detecting the marker TY3-M3 may respectively consists of the sequences 5'-AGC-TATCAGCTGCCAGAGACAT-3' (SEQ ID NO: 7) and 5'-CACCATCATTGTATCCAGAGAGC-3' (SEQ ID NO: 8).

In a preferred embodiment, the PCR comprises an initial denaturation step followed by cycles of denaturation-annealing-elongation steps and a final elongation step.

The initial denaturation step may be performed under heating conditions ranging from 90° C. to 105° C., during 15 s to 15 min. Preferably, the heating conditions range from 92° C. to 102° C., more preferably from 94° C. to 100° C., still more preferably the heating conditions are at 94° C. Preferably, the initial denaturation step is performed during 1 min to 15 min, more preferably during 8 min to 12 min, still more preferably during 5 min to 10 min, and still more preferably the initial denaturation step is performed during 5 min. In a preferred embodiment, the initial denaturation step is performed at 94° C. during 5 min.

Each cycle of denaturation-annealing-elongation step includes a denaturation phase under heating conditions, followed by an annealing phase performed under conditions which allow the hybridization of the primers and the probe to the sequence to be amplified, and an elongation phase performed under conditions which allow the polymerase to synthesizes an extension product from each primer that is annealed to the sequence to be amplified.

The denaturation phase may be performed between 90° C. to 105° C., preferably 92° C. to 100° C., more preferably between 94° C. to 98° C., during 10 s to 4 min, preferably during 10 s to 2 min, more preferably during 15 s to 1 min.

The annealing phase may be performed between 35° C. and 70° C., preferably between 40° C. to 65° C., more preferably between 45° C. to 60° C., still more preferably between 50° C. to 60° C., during 10 s to 2 min, preferably during 20 s to 1.5 min, more preferably during 25 s to 1 min.

The elongation phase may be performed between 40° C. and 80° C., preferably between 50° C. to 75° C., more preferably between 55° C. to 72° C., during 10 s to 5 min, preferably during 20 s to 3 min, more preferably during 30 s to 1 min.

In a preferred embodiment, the denaturation phase is performed at 94° C. during 50 s, the annealing phase is performed at 56° C. during 1 min and the elongation phase is performed at 72° C. during 50 s. The denaturation-annealing-elongation step may be repeated during 30 to 50 cycles, preferably during 35 to 45 cycles. Still more preferably, the denaturation-annealing-elongation step is repeated during 35 cycles.

The final elongation step may be performed under heating conditions ranging from 60° C. to 90° C., during 15 s to 15 min. Preferably, the heating conditions range from 65° C. to 80° C., more preferably from 70° C. to 80° C. Preferably, the final elongation step is performed during 1 min to 15 min, more preferably during 8 min to 12 min, still more preferably during 5 min to 10 min. In a preferred embodiment, the final elongation step is performed at 72° C. during 10 min.

In some embodiments, detection of the TO-0178067 marker is performed by PCR using the touchdown method in which the elongation and annealing steps are incorporated into a single step. The temperature used for the annealing stage determines the specificity of the reaction and hence the ability of the primers to anneal to the DNA template. A touchdown PCR involves a first step of Taq polymerase activation, followed by a second step called the touchdown step that involves a high annealing temperature and incrementally decreasing the annealing temperature in each PCR cycle, and a third step of DNA amplification. The higher annealing temperatures in the early cycles of a touchdown ensure that only very specific base pairing will occur between the DNA and the primer, hence the first sequence to be amplified is most likely to be the sequence of interest. The annealing temperature is gradually decreased to increase the efficiency of the reaction. The regions that were originally amplified during the highly specific early touchdown cycles will be further amplified and outcompete any non-specific amplification that may occur at the lower temperatures.

In particular, detection of the marker TO-0178067 is performed using two forward primers, one being specific for the resistant allele and one being specific for the susceptible allele, and one common reverse primer. For example, the forward primer for detecting the susceptible allele of marker TO-0178067 may consist of the sequence 5'-GAAGGTGACCAAGTT-CATGCTTTTGTTCCCCCAGCTGAGAGG-3' (SEQ ID NO: 4), the forward primer for detecting the resistant allele of TO-0178067 marker may consist of the sequence 5'-GAAGGTCGGAGTCAACGGAT-TCTTTTGTTCCCCCAGCTGAGAGA-3' (SEQ ID NO: 5), and the common reverse primer may consist of the sequence 5'-GACCAACACGKCCTACGAGGTA-3' (SEQ ID NO: 6).

In a preferred embodiment, the first step of Taq polymerase activation may be performed under heating conditions ranging from 90° C. to 105° C., during 10 min to 20 min. Preferably, the heating conditions range from 92° C. to 102° C., more preferably from 93° C. to 98° C., still more preferably the heating conditions are at 94° C. Preferably, the Taq polymerase activation step is performed during 10 min to 18 min, more preferably during 13 min to 15 min, still more preferably the initial denaturation step is performed during 15 min. In a preferred embodiment, the Taq polymerase activation step is performed at 94° C. during 15 min.

In a preferred embodiment, the touchdown step may be performed with a high annealing temperature ranging from 90° C. to 105° C., during 1 s to 30 s, followed by an annealing temperature ranging from 60° C. to 70° C., during 15 s to 90 s. Preferably, the touchdown step may be performed with a high annealing temperature at 94° C., during 20 s, followed by an annealing temperature at 65° C. during 60 s. The touchdown step may be repeated during 5 to 25 cycles, preferably during 10 cycles, with an incrementally decrease of the annealing temperature between 0.5° C. to 1° C. per cycle leading to a final annealing temperature ranging from 35° C. to 67° C. Preferably the touchdown step may be performed with a high annealing temperature at 94° C. during 20 s, followed by an annealing temperature at 65° C. during 60 s with an incrementally decrease of the annealing temperature of 0.8° C. per cycle leading to a final annealing temperature at 57° C. after 10 cycles.

In a preferred embodiment, the third step of DNA amplification may be performed in two rounds with a first round at a temperature ranging from 90° C. to 105° C., during 1 s to 40 s, followed by a second round at a temperature ranging from 50° C. to 70° C., during 1 s to 90 s. Preferably the first round may be performed at a temperature ranging from 92° C. to 98° C., during 15 s to 30 s. Preferably the second round may be performed at a temperature ranging from 55° C. to 65° C., during 40 s to 65 s. Still preferably, the third step of DNA amplification may be performed in two rounds with a first round at a temperature of 94° C. during 20 s, followed by a second round at a temperature of 57° C. during 60 s. The third step of DNA amplification may be repeated during 20 to 45 cycles, preferably during 15 to 35 cycles. Still more preferably, the third step of DNA amplification is repeated during 26 cycles.

In some embodiments, detection of the markers SSR-OL4, TY3-M3, and TO-0178067 is performed as disclosed in the examples of the present application.

In some embodiments, detection of the marker Mi2.3 is performed by PCR using the touchdown method in which the elongation and annealing steps are incorporated into a single step. The temperature used for the annealing stage determines the specificity of the reaction and hence the ability of the primers to anneal to the DNA template. A touchdown PCR involves a first step of Taq polymerase activation, followed by a second step called the touchdown step that involves a high annealing temperature and incrementally decreasing the annealing temperature in each PCR cycle, and a third step of DNA amplification. The higher annealing temperatures in the early cycles of a touchdown ensure that only very specific base pairing will occur between the DNA and the primer, hence the first sequence to be amplified is most likely to be the sequence of interest. The annealing temperature is gradually decreased to increase the efficiency of the reaction. The regions that were originally amplified during the highly specific early touchdown cycles will be further amplified and outcompete any non-specific amplification that may occur at the lower temperatures.

In particular, detection of the marker Mi2.3 is performed using two forward primers, one being specific for the resistant allele and one being specific for the susceptible allele, and one common reverse primer. For example, the forward primer for detecting the resistant allele of marker Mi2.3 may consist of the sequence 5'-GAAGGTCGGAGT-CAACGGATTCGACGGAACTATTAAGTAGACGAG-3' (SEQ ID NO: 10), the forward primer for detecting the susceptible allele of marker Mi2.3 marker may consist of the sequence 5'-GAAGGTGACCAAGTTCATGCTCGACG-GAACTATTAAGTAGACGAC-3' (SEQ ID NO: 11), and the common reverse primer may consist of the sequence 5'-AACTGMTTTGGTTGCTTGTTATTTTACTAA-3' (SEQ ID NO: 12).

In a preferred embodiment, the first step of Taq polymerase activation may be performed under heating conditions ranging from 90° C. to 105° C., during 10 min to 20 min. Preferably, the heating conditions range from 92° C. to 102° C., more preferably from 93° C. to 98° C., still more preferably the heating conditions are at 94° C. Preferably, the Taq polymerase activation step is performed during 10 min to 18 min, more preferably during 13 min to 15 min, still more preferably the initial denaturation step is performed during 15 min. In a preferred embodiment, the Taq polymerase activation step is performed at 94° C. during 15 min.

In a preferred embodiment, the touchdown step may be performed with a high annealing temperature ranging from 90° C. to 105° C., during 1 s to 30 s, followed by an annealing temperature ranging from 60° C. to 70° C., during 15 s to 90 s. Preferably, the touchdown step may be performed with a high annealing temperature at 94° C., during 20 s, followed by an annealing temperature at 65° C.

during 60 s. The touchdown step may be repeated during 5 to 25 cycles, preferably during 10 cycles, with an incrementally decrease of the annealing temperature between 0.5° C. to 1° C. per cycle leading to a final annealing temperature ranging from 35° C. to 67° C. Preferably the touchdown step may be performed with a high annealing temperature at 94° C. during 20 s, followed by an annealing temperature at 65° C. during 60 s with an incrementally decrease of the annealing temperature of 0.8° C. per cycle leading to a final annealing temperature at 57° C. after 10 cycles.

In a preferred embodiment, the third step of DNA amplification may be performed in two rounds with a first round at a temperature ranging from 90° C. to 105° C., during 1 s to 40 s, followed by a second round at a temperature ranging from 50° C. to 70° C., during 1 s to 90 s. Preferably the first round may be performed at a temperature ranging from 92° C. to 98° C., during 15 s to 30 s. Preferably the second round may be performed at a temperature ranging from 55° C. to 65° C., during 40 s to 65 s. Still preferably, the third step of DNA amplification may be performed in two rounds with a first round at a temperature of 94° C. during 20 s, followed by a second round at a temperature of 57° C. during 60 s. The third step of DNA amplification may be repeated during 20 to 45 cycles, preferably during 15 to 35 cycles. Still more preferably, the third step of DNA amplification is repeated during 26 cycles.

According to a preferred embodiment, the detection and/or selection is made on the basis of the alleles of the markers SSR-L4, TO-0178067, TY3-M3 and Mi23 as described in the first aspect of the invention. Preferably, the detection and/or selection is thus made on the presence of one or more of the following alleles: an allele of 382 bp of the marker SSR-OL4, an allele A of the marker TO-0178067 on chromosome 6, an allele of 220 bp of the marker TY3-M3, and an allele C of the marker Mi2.3. Still preferably, the detection and/or selection is thus made on the presence of the combination of alleles 1, 2 or 3 as described in the first aspect of the invention.

In addition to introgression of the OL4 and TY1 genes conferring resistance to TYLCV, PM and nematodes, as detailed in the methods of the invention, said genes can also be introduced into S. lycopersicum background by genetic engineering in order to obtain a commercial S. lycopersicum plant resistant to TYLCV, PM and nematodes. The identification and cloning of the introgressed resistance OL4 and TY1 genes from S. lycopersicum conferring the desired phenotype, inter alia from the deposit, are routine for the skilled person.

According to a further aspect, the present invention is also directed to hybrid plant of S. lycopersicum which is resistant to Tomato Yellow Leaf Curl Virus (TYLCV), powdery mildew (PM) and nematodes, obtainable by crossing a resistant plant according to the first aspect of the invention, or a resistant plant obtainable by the method disclosed according to the fourth aspect, with a plant of S. lycopersicum, for example a plant susceptible to TYLCV, PM and nematodes, or a plant with a different level of resistance to TYLCV, PM and nematodes. In some embodiments, hybrid plant may comprise the Mi-1 gene conferring resistance to nematodes in trans on chromosome 6. By "Mi-1 gene conferring resistance to nematodes in trans on chromosome 6", it is meant that the Mi-1 gene conferring resistance to nematodes is not on the same coupling phase than the resistance OL4 and TY1 genes, i.e. that the Mi-1 gene conferring resistance to nematodes is not on the same chromosome as the resistance OL4 and TY1 genes. In other word, said hybrid plant may comprise the resistance OL4 and TY1 genes in coupling phase on chromosome 6, without having the Mi-1 gene conferring resistance to nematodes in said coupling phase, but having the Mi-1 gene conferring resistance to nematodes in trans on the homologous chromosome 6.

In a further aspect, the invention relates to a method for the production of S. lycopersicum plantlets or plants resistant to Tomato Yellow Leaf Curl Virus (TYLCV), powdery mildew (PM) and nematodes, which method comprises:

a) culturing in vitro an isolated cell or tissue from a S. lycopersicum plant of the invention to produce S. lycopersicum micro-plantlets resistant to Tomato Yellow Leaf Curl Virus (TYLCV), powdery mildew (PM) and nematodes, and b) optionally further subjecting the S. lycopersicum micro-plantlets to an in vivo culture phase to develop into S. lycopersicum plant resistant to Tomato Yellow Leaf Curl Virus (TYLCV), powdery mildew (PM) and nematodes.

The isolated cell or tissue used to produce a micro-plantlet is an explant obtained under sterile conditions from a parent S. lycopersicum plant of the invention to be propagated. The explant comprise or consist, for instance, of a cotyledon, hypocotyl, stem tissue, leaf, embryo, meristem, node bud, shoot apice, or protoplast. The explant can be surface sterilized before being placed on a culture medium for micropropagation.

Conditions and culture media that can be suitably used in plant micropropagation are well known to those skilled in the art of plant cultivation and are described, for example, in "Plant Propagation by Tissue Culture, Handbook and Directory of Commercial Laboratories, eds. Edwin F George and Paul D Sherrington, Exegetics Ltd, 1984".

Micropropagation Typically Involves (i) axillary shoot production: axillary shoot proliferation is induced by adding cytokinin to the shoot culture medium, to produce shoots preferably with minimum callus formation;

(ii) adventitious shoot production: addition of auxin to the medium induces root formation, in order to produce plantlets that are able to be transferred into the soil. Alternatively, root formation can be induced directly into the soil.

Plantlets can be further subjected an in vivo culture phase, by culture into the soil under lab conditions, and then progressive adaptation to natural climate, to develop into S. lycopersicum plant resistant to Tomato Yellow Leaf Curl Virus (TYLCV), powdery mildew (PM) and nematodes.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Seed Deposit

A representative sample of seeds from the S. lycopersicum plant according to the invention (i.e. seeds from TCR1 plant) has been deposited by H M. Clause, S. A., Rue Louis Saillant, Z. I. La Motte, BP83, 26802 Portes-lès-Valence cedex, France, pursuant to, and in satisfaction of, the requirements of the Budapest Treaty on the International Recognition of the Deposit of Microorganisms for the Purposes of Patent Procedure (the "Budapest Treaty") with the National Collection of Industrial, Food and Marine Bacteria (NCIMB), 23 St Machar Drive, Aberdeen, Scotland, AB21 9YA, United Kingdom, on Nov. 19, 2015, under accession number 42490.

A deposit of the TCR1 seeds is maintained by H M. Clause, S. A., Rue Louis Saillant, Z. I. La Motte, BP83, 26802 Portes-Ibs-Valence cedex, France.

SEQUENCE LISTING

SEQ ID NO: 1 shows the sequence of a forward primer for SSR-L4 marker detection.

SEQ ID NO: 2 shows the sequence of a reverse primer for SSR-L4 marker detection.

SEQ ID NO: 3 shows a flanking sequence of the marker TO-0178067.

SEQ ID NO: 4 shows the sequence of a forward primer for detecting the susceptible allele of TO-0178067 marker.

SEQ ID NO: 5 shows the sequence of a forward primer for detecting the resistant allele of TO-0178067 marker.

SEQ ID NO: 6 shows the sequence of a common reverse primer for TO-0178067 marker detection.

SEQ ID NO: 7 shows the sequence of a forward primer for TY3-M3 marker detection.

SEQ ID NO: 8 shows the sequence of a reverse primer for TY3-M3 marker detection.

SEQ ID NO: 9 shows a flanking sequence of the marker Mi2.3.

SEQ ID NO: 10 shows the sequence of a forward primer for detecting the resistant allele of Mi2.3 marker.

SEQ ID NO: 11 shows the sequence of a forward primer for detecting the susceptible allele of Mi2.3 marker.

SEQ ID NO: 12 shows the sequence of a common reverse primer for Mi2.3 marker detection.

EXAMPLES

Figure 1:
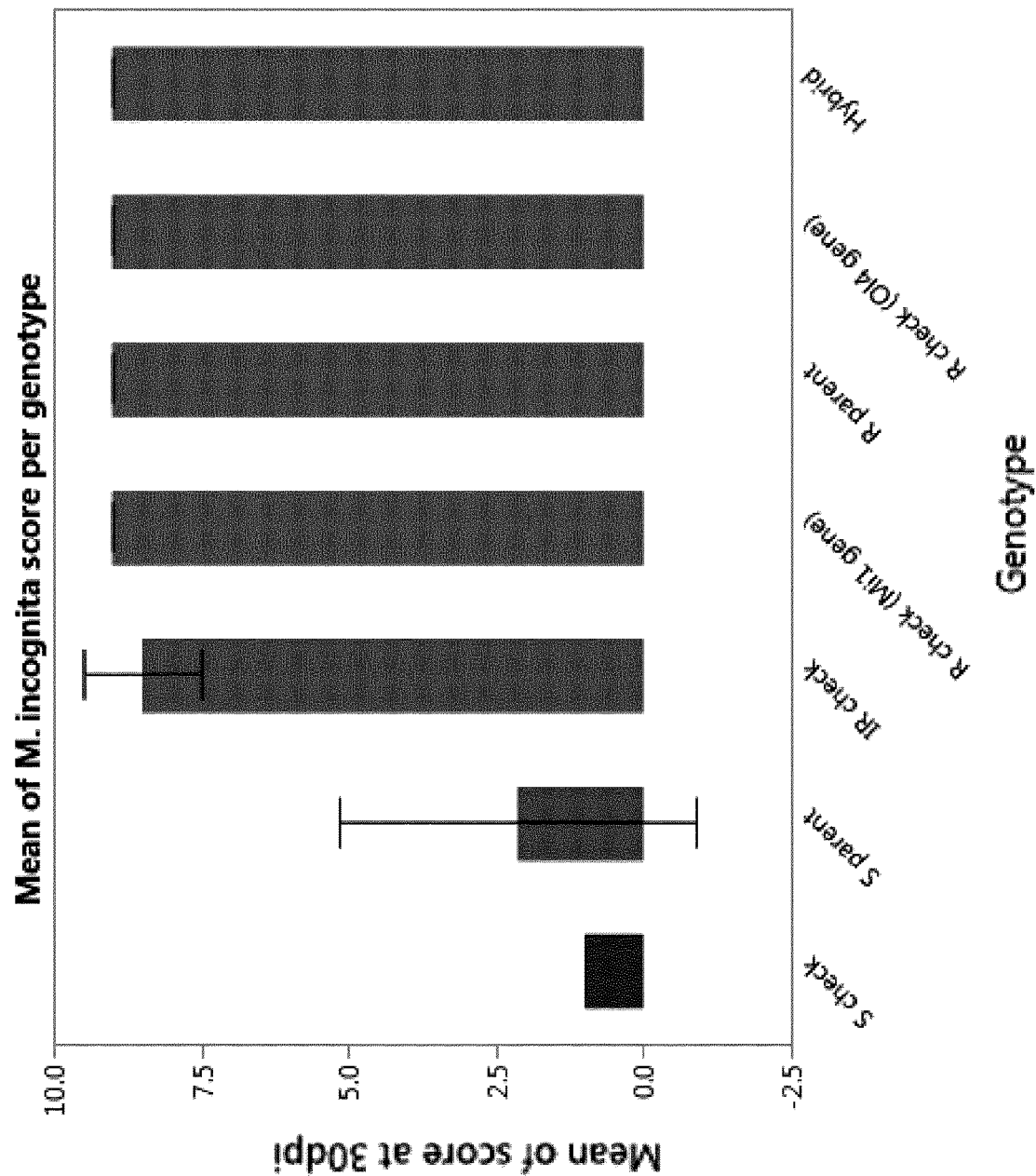
FIG. 1 depicts the pathological test of the MTR line and TCR1 hybrid for Nematode *M. incognita* resistance. The rating scale is as described in paragraph 1.3 of the examples. S check=susceptible check, S parent=susceptible parent, IR check=Intermediate resistant check, R check (Mi-1 gene) =resistant check harboring the Mi-1 gene conferring resistance to nematodes in its genome, R parent=MTR, R check (014 gene)=resistant check harboring the OL4 gene conferring resistance to PM and nematodes, Hybrid=TCR1. Each error bar is constructed using 1 standard deviation from the mean.

1. Material and Methods
1.1. *Oidium* Test (Controlled Conditions)
*Oidium neolycopersici* Production

*O. neolycopersici* used in this work was collected from naturally infected tomato plants in Saint-Remy de Provence. This isolate was maintained on susceptible tomato plants and transferred on new plants every four weeks during all the test season. Plants were grown in a growth chamber adjusted to 24° C. day, 20° C. night with a 14 h photoperiod and a relative humidity of 75% (±5%).

Plant Material Production

Plants are sowed in flats with soil. Two weeks after sowing, plantlets are transplanted in trays of 24 cells (1 cell=5.5×6 cm) with 1 plant per cell.

Experimental Procedure and Evaluation

Plants at stage 3-4 leaves (between 21 to 28 days after sowing) are inoculated by spraying the upper side of leaves with a suspension of between 1.104 and 1.105 conidia per ml. The inoculum was prepared by washing conidial spore from infected leaves with water. The inoculum solution was used immediately. Plants were grown in a growth chamber adjusted to 24° C. day, 20° C. night with a 14 h photoperiod and a relative humidity of 75% (±5%).

Test is evaluated between 10 and 20 days (e.g. 14 days) according of the level of infection of the susceptible check. The *O. neolycopersici* growth was evaluated by the percentage of leaves area with sporulation using the following reading scale: 9=no sporulation; 8=slight sporulation with 1% to 5% of leave area infected; 7=moderate sporulation with leave area infected between 6% and 25%; 5=moderate sporulation with leave area infected between 26% and 50%; 3=strong sporulation with leave area infected between 51% and 75%; 1=very strong sporulation with more than 75% of leave area infected.

1.2. TYLCV Test
TYLCV Inoculum

The TYLCV inoculum is obtained from the EELM-CSIC (Estacion Experimental la Mayora e Instituto de Hortofruticultura Subtropical, Malaga) in the form of infected whiteflies.

Plant Material Production

Plants are sowed in packs of 24 holes and growth of plantlets is done at nursery or inside the module where they will be tested, i.e. in any case in a space free of insects to avoid cross-contamination with the test. The number of plants to test per genotypes depends on each experiment, but 350-360 plants at most can be tested in each experiment. For each experiment, one susceptible check, one intermediate resistant check, and one resistant check are sown and inoculated.

Experimental Procedure and Evaluation 12-14 days old plants (2 true leaves stage) are used for the experiment. Packs of plants with tested genotype and checks are placed at random inside an insect-proof glasshouse. Transmission of the virus is performed by releasing infected whiteflies inside the glasshouse during 2 days under the following conditions: 26-28° C. during the day and 20° C. at night. Then whiteflies are killed using insecticide application under the following conditions: 30-32° C. during the day and 18-20° C. at night. One day after insecticide application, plants are taken out of the box and the absence of whiteflies is checked.

Three weeks after inoculation (or four weeks after inoculation if the reading at 3 weeks is not clear), plants are harvested and the TYLCV infection is evaluated according to the following scale: 9=No symptoms, 8=slight symptoms in a close inspection with slight veins discoloration on edge of apical leaves; 6=slight symptoms on apical part of the plant and minor curling; 5=moderate yellowing, curling and cupping on apical leaves with a plant growth that continues normally; 3=strong symptoms with yellowing, curling and cupping with moderate dwarfism; and 1=very strong symptoms on apical part with yellowing, curling and cupping with severe dwarfism, and leaflet with strong size reduction and non-developed.

1.3. Nematodes Test (Controlled Conditions)

Nematode Material Production

The *M. incognita* and *M. javanica* isolates used in this work are independently maintained as living organism in susceptible Tomato plants. Every 8-10 months (depending on the season), nematodes isolates are transferred to new Tomato plants. The two isolates are maintained in two different greenhouses to avoid cross contamination.

Plant Material Production

Plants are sowed in flats with sand/soil mix (50/50). In each flat, there is 5 rows of 12 plants, 2 raws/genotype plus 1 row with 6 plants of each check. The susceptible check is Porphyre and the resistant check is Annabelle carrying Mi1 gene conferring resistance to nematodes. For each genotype, 12 plants were tested in 3 repetitions.

Experimental Procedure and Evaluation:

For each experiment, 18-21 days old plants (2-4 leaves stage) were inoculated with infected roots obtained from the nematode production. Inoculation with infected roots is performed by cutting said infected roots in small segments and burying them between each plants row to be tested. The experiments were conducted in greenhouse with a temperature around 24° C. (±3). Four weeks after inoculation, plants are harvested and the nematode infection is evaluated by observation of the numbers of galls present on the whole root system of each plant. Plants are individually evaluated according to the following reading scale: 9=no galls; 7=between 1% and 30% of galls with limited size on root system; 5=more than 30% of galls on root system; 3=at least 60% of galls on root system; 1=at least 90% of galls on root system. A genotype is considered as (i) resistant if all the plants are in class 9, (ii) intermediate resistant if all the plants are in class 7 and/or 5, and (iii) susceptible if all the plants are in class 3 and/or 1.

1.4. DNA Extraction and Genotyping Protocol

The plant DNA extraction was realized using the protocol described in Dellaporta et al., 1983, Plant Molecular Biology Reporter, Vol. 1, Issue 4, 19-21. The precipitation and cleaning steps were done with isopropanol and ethanol 70% solutions, respectively.

For SSR-OL4 marker detection, the DNA (5 µL, 1/10 dilution) was pooled with a reactional volume of 10 µL containing MgCl$_2$ (2.5 mM), dNTP (0.25 mM), buffer (1×), primers (0.025 µM for the forward primer and 0.1 µM for the reverse primer) and the Taq Polymerase (0.5 U) (Invitrogen™). The forward primer and the reverse primer for detecting the SSR-OL4 marker respectively consist of the sequences 5'-GAAATCGCAGAGTCACACTT-3' (SEQ ID NO: 1) and 5'-ATCCCGTGTAATTAATCGAA-3' (SEQ ID NO: 2). The thermal cycling conditions for SSR-OL4 marker detection comprised (i) an initial denaturation step at 95° C. for 5 min, (ii) 10 cycles at 95° C. for 15 s and 57° C. for 15 s and 72° C. for 30 s, (iii) 25 cycles at 95° C. for 15 s and 52° C. for 15 s and 72° C. for 30 s, and (iv) an elongation step at 72° C. for 10 min. Then, PCR products were injected in an ABI 3730 sequencer and the SSR profiles were analysed with the Genemaper.

For TY3-M3 marker detection, the DNA (5 µL, 1/10 dilution) was pooled with a reactional volume of 5 µL containing MgCl$_2$ (2.5 mM), dNTP (2.5 mM), buffer (1×), primers (0.2 µM) and the Taq Polymerase (0.5 U) (Invitrogen™). The forward primer and the reverse primer for detecting the TY3-M3 marker respectively consists of the sequences 5'-AGCTATCAGCTGCCAGAGACAT-3' (SEQ ID NO: 7) and 5'-CACCATCATTGTATCCAGAGAGC-3' (SEQ ID NO: 8). The thermal cycling conditions comprised (i) an initial denaturation step at 94° C. for 5 min, (ii) 35 cycles at 94° C. for 50 s and 56° C. for 60 s and 72° C. for 50 s, and (iii) an elongation step at 72° C. for 10 min. Then, 5 µL of PCR products were digested with Mse1 restriction enzyme. The final products were loaded on 2% agarose gel.

TO-0178067 and Mi2.3 markers detection is performed using the KASPar™ technology. KASPar™ primers were designed using PrimerPicker™ tool in KLIMS™ (KBioscience Laboratory Management System) by providing DNA sequences with SNPs. Three primers, A1 (Allele specific primer 1), A2 (Allele specific primer 2), and C (common reverse primer) were designed for each SNP sequence based on KASPar™ chemistry. DNA strand and allele designation and orientation is done according to the TOP/BOT method developed by Illumina (illumina.com/documents/products/technotes/technote_topbot.pdf).

More specifically, the three primers for detecting the marker TO-0178067 respectively consist of the sequences: 5'-GAAGGTGACCAAGTT-CATGCTTTTGTTCCCCCAGCTGAGAGG-3' (SEQ ID NO: 4, primer A1 specific for the susceptible allele), 5'-GAAGGTCGGAGTCAACGGAT-TCTTTTGTTCCCCCAGCTGAGAGA-3' (SEQ ID NO: 5, primer A2 specific for the resistant allele), and 5'-GAC-CAACACGKCCTACGAGGTA-3' (SEQ ID NO: 6, common reverse primer C).

More specifically, the three primers for detecting the marker Mi2.3 respectively consists of the sequences: 5'-GAAGGTGACCAAGTTCATGCTCGACGGAACTAT-TAAGTAGACGAC-3' (SEQ ID NO: 11, primer A1 specific for the susceptible allele), 5'-GAAGGTCGGAGTCAACG-GATTCGACGGAACTATTAAGTAGACGAG-3' (SEQ ID NO: 10, primer A2 specific for the resistant allele), and 5'-AACTGMTTTGGTTGCTTGTTATTTTACTAA-3' (SEQ ID NO: 12, common reverse primer C).

An assay mix of each KASPar™ reaction was prepared as in the KASPar™ SNP Genotyping System v2.0. The final reaction volume was 2 µL, per reaction, including 1 µL DNA template (5 ng/µL), 0.98 µL Kaspar Reaction mix v4, 0.014 µL Assay mix (6:6:15 ratio of primers A1:A2:C). The assay was carried out in 1536-well format. The thermal cycling conditions used during the assay were according to the manufacturer's instructions: 94° C. for 15 minutes; 10 cycles of 94° C. for 20 s, 65° C. for 60 s with −0.8° C. per cycle; and 26 cycles of 94° C. for 20 s, 57° C. for 60 s. PCR plates were centrifuged, and allele-specific FAM and VIC intensities were read on a PHERAstar® spectrofluorometer (BMG LaBTech) at room temperature. Data were directly loaded and analyzed on KLIMS™ using KlusterCaller™.

2. Combination in Cis of the OL4 and TY1 Genes

On spring of the first year, a line "A" homozygous for the TY1 gene conferring resistance to TYLCV (tested with marker TY3-M3) was crossed with the line "B" carrying the OL4 gene conferring resistance to PM and nematodes at heterozygous state.

Then 4 heterozygous plants for the resistance TY1 and OL4 genes were selected using the TY3-M3 and SSR-OL4 markers and crossed in autumn of the second year with a line "C" not carrying the resistance OL4 and TY1 genes.

Among the 500 plants obtained from this last cross, only 5 plants were found heterozygous for the resistance OL4 and TY1 genes using the markers SSR-OL4 and TY3-MY3 described in example 1.4. These 5 plants correspond to the recombinant Ol4/Ty1, i.e. plants carrying the resistance OL4 and TY1 genes in coupling phase on chromosome 6.

These 5 plants were selfed in spring of the fourth year. Their progeny were tested for the presence of the resistance TY1 and OL4 genes. Homozygous plants were selected. The progeny was tested in Jordania for TYLCV resistance in natural conditions. The results in Table 4 show a resistant level for the progeny carrying the resistance OL4 and TY1 genes at homozygous state.

TABLE 4

Field test in natural condition of the progeny carrying the resistance OL4 and TY1 genes at homozygous state for TYLCV resistance.

| | Number of plants tested | TYLCV rating | Interpretation |
|---|---|---|---|
| Susceptible check | 10 | 1 | Susceptible |
| Resistant check | 10 | 7 | Resistant |
| Progeny Ol4/Ty1 | 10 | 7 | Resistant |

The natural infection rating scale is as follow: 1 = very susceptible, 3 = susceptible, 5 = intermediate resistant, 7 = resistant, 9 = strongly resistant.

On the third year the recombinant Ol4/Ty1 was back-crossed in different backgrounds. More particularly, the recombinant Ol4/Ty1 has been back-crossed with the line MGN carrying the Mi-1 gene conferring resistance to nematodes, with the aim to replace said Mi-1 gene with the Ol4/Ty1 combination. After 4 cycles of selfing and selection using the markers SSR-OL4 and TY3-MY3, one line called MTR carrying the resistance OL4 and TY1 genes in coupling phase, but not carrying the Mi-1 gene conferring resistance to nematodes in said coupling phase, was identified and kept to make hybrids, such as the TCR1 hybrid, with good agronomical value.

A genetic analysis demonstrated that the MTR line and TCR1 hybrid harbor the resistance OL4 and TY1 genes respectively at homozygous state and heterozygous state without harboring the Mi-1 gene conferring resistance to nematodes (Table 5).

TABLE 5

Genetic analysis of MTR line and TCR1 hybrid.

| Marker | Susceptible check | MTR line | TCR1 |
|---|---|---|---|
| Mi2.3 | C/C | C/C | C/C |
| SSR-OL4 | 389 bp/389 bp | 382 bp/382 bp | 382 bp/389 bp |
| TY3-M3 | 160 pb/160 pb | 220 bp/220 bp | 220 bp/160 bp |
| TO-0178067 | G/G | A/A | A/G |

Said genetic analysis thus demonstrated that the TCR1 hybrid comprises the following combination of alleles:
(i) an allele of 220 bp of the marker TY3-M3 and an "allele A" of the TO-0178067 marker, an allele of 382 bp of the marker SSR-OL4, and an "allele C" of the marker Mi2.3 physically located on the first homologous chromosome 6, and
(ii) an allele of 160 bp of the marker TY3-M3 and an "allele G" of the TO-0178067 marker, an allele of 389 bp of the marker SSR-OL4, and an "allele C" of the marker Mi2.3 physically located on the second homologous chromosome 6.

Figure 2:
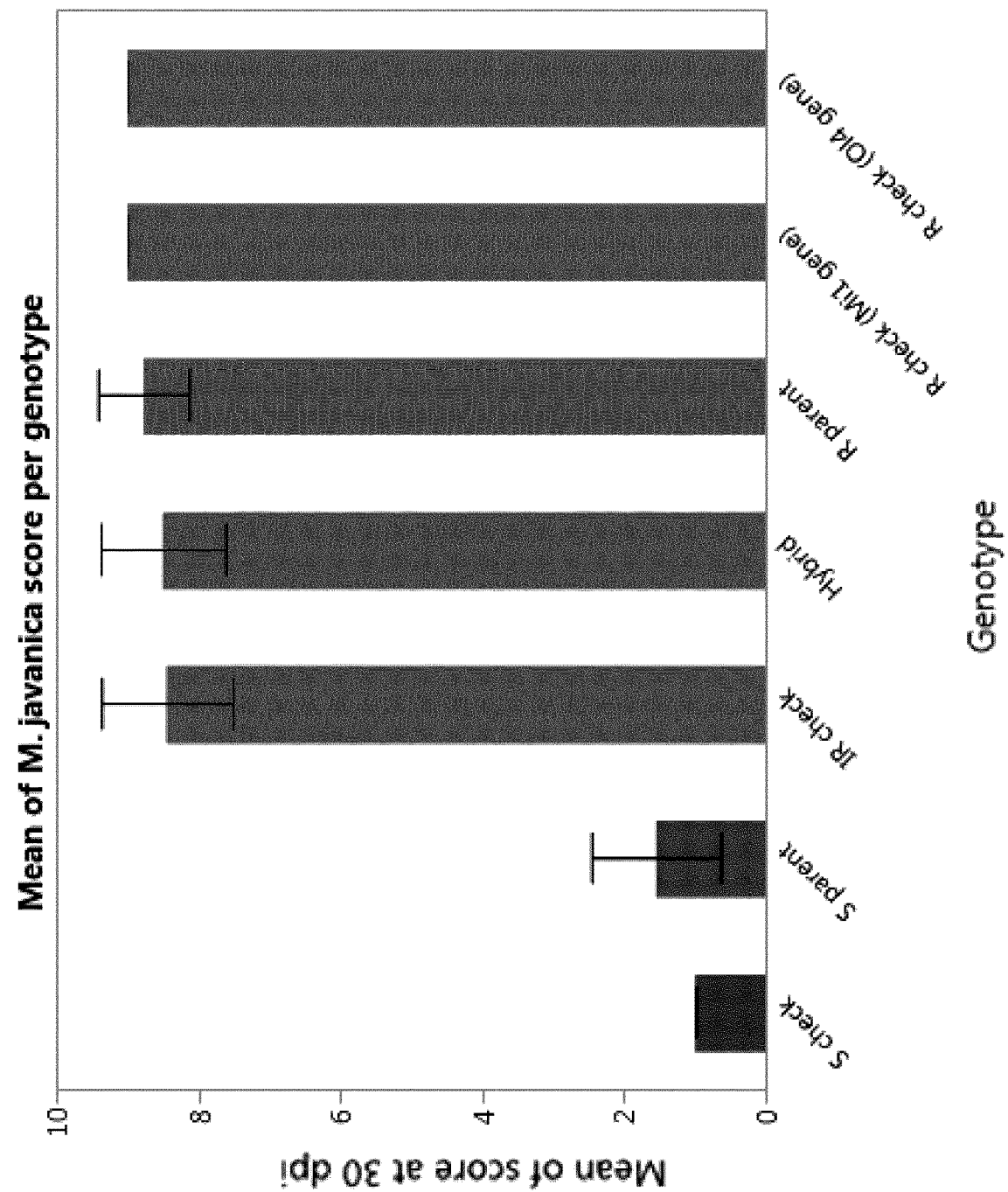
FIG. 2 depicts the pathological test of the MTR line and TCR1 hybrid for Nematode *M. javanica* resistance. The rating scale is as described in paragraph 1.3 of the examples. S check=susceptible check, S parent=susceptible parent, IR check=Intermediate resistant check, R check (Mi-1 gene) =resistant check harboring the Mi-1 gene conferring resistance to nematodes in its genome, R parent=MTR, R check (014 gene)=resistant check harboring the OL4 gene conferring resistance to PM and nematodes, Hybrid=TCR1. Each error bar is constructed using 1 standard deviation from the mean.
Figure 3:
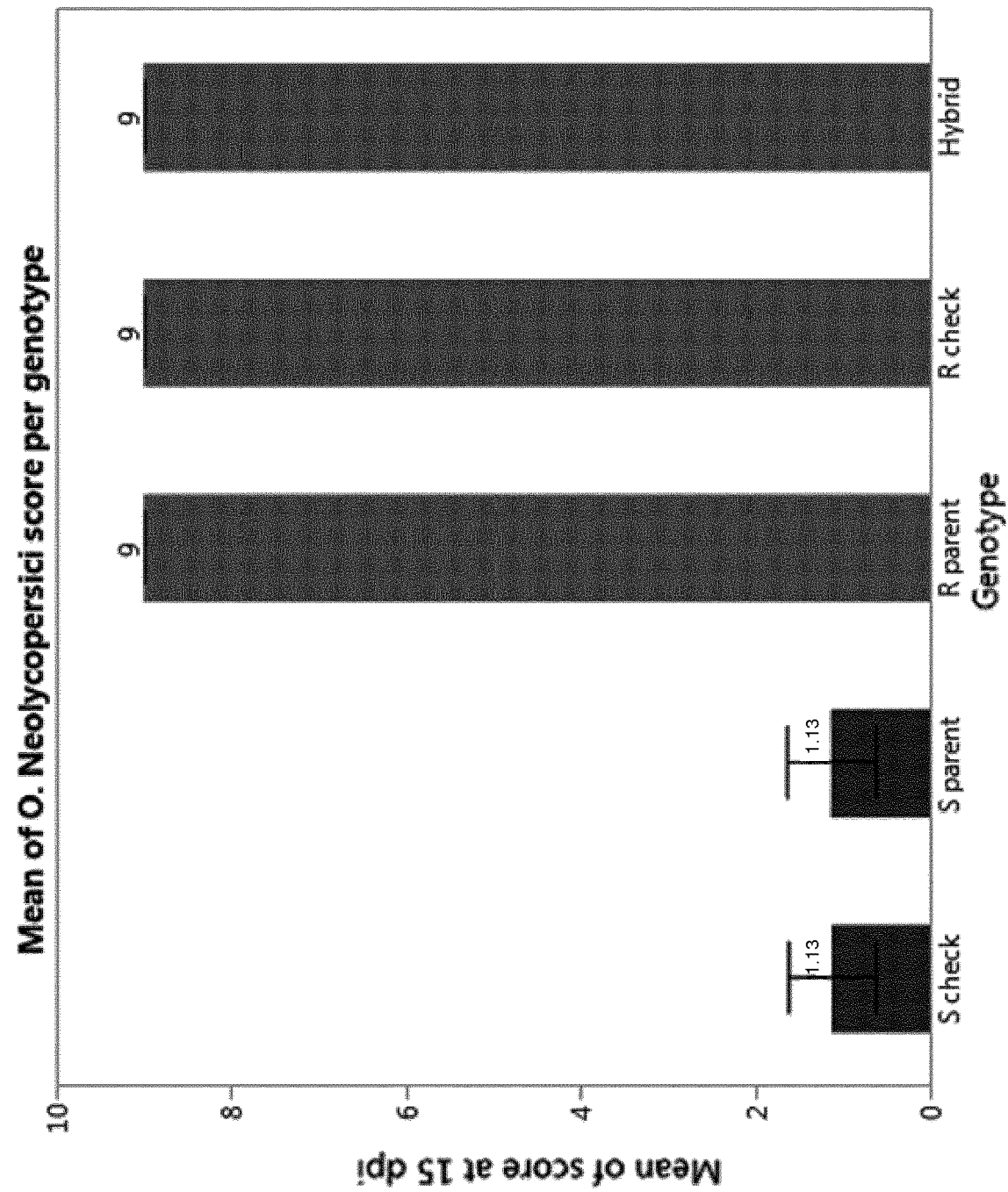
FIG. 3 depicts the pathological test of the MTR line and TCR1 hybrid for 0. neolycopersici resistance. The rating scale is as described in paragraph 1.1 of the examples. S check=susceptible check, S parent=susceptible parent, R check=resistant check, R parent=MTR, Hybrid=TCR1. Each error bar is constructed using 1 standard deviation from the mean.
Figure 4:
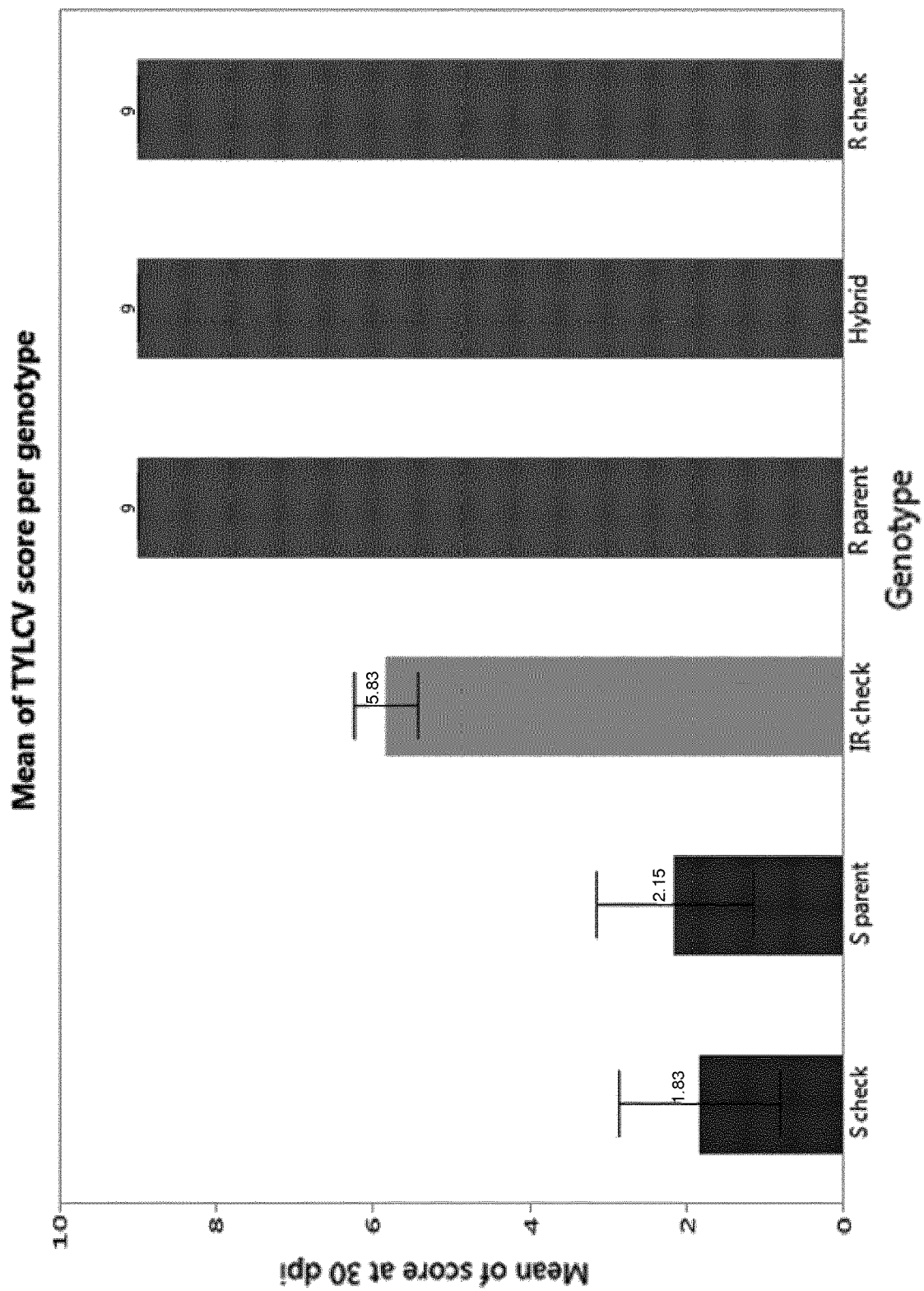
FIG. 4 depicts the pathological test of the MTR line and TCR1 hybrid for TYLCV resistance. The rating scale is as described in paragraph 1.2 of the examples. S check=susceptible check, S parent=susceptible parent, IR check=intermediate resistant check, R check=resistant check, R parent=MTR, Hybrid=TCR1. Each error bar is constructed using 1 standard deviation from the mean.

The MTR line and the TCR1 hybrid have then been tested for their resistance to TYLCV, PM and nematodes using the above described tests (see examples 1.1 to 1.3). Results of the tests are presented in FIGS. 1 to 4. The results demonstrated that the MTR line and the TCR1 hybrid are resistant to *O. neolycopersici*, TYLCV and to the two nematode species *M. incognita* and *M. javanica*.

3. Genetic Modification of Tomato Seeds by Ethyl Methane Sulfonate (EMS)

Seeds of a tomato varieties are to be treated with EMS by submergence of approximately 2000 seeds per variety into an aerated solution of either 0.5% (w/v) or 0.7% EMS for 24 hours at room temperature.

Approximately 1500 treated seeds per variety per EMS dose are germinated and the resulting plants are grown, preferably in a greenhouse, for example, from May to September, to produce seeds.

Following maturation, M2 seeds are harvested and bulked in one pool per variety per treatment. The resulting pools of M2 seeds are used as starting material to identify the individual M2 seeds and the plants resistant to TYLCV, PM and nematodes.

The invention claimed is:

1. A *Solanum lycopersicum* (*S. lycopersicum*) plant that is resistant to Tomato Yellow Leaf Curl Virus (TYLCV), powdery mildew (PM) and nematodes, wherein said plant comprises (i) an allele of OL4 gene conferring resistance to PM and nematodes and (ii) an allele of TY/gene conferring resistance to TYLCV in coupling phase on chromosome 6, and wherein said plant, if it comprises an allele of Mi-1 gene conferring resistance to nematodes then said allele of Mi-1 gene conferring resistance to nematodes is not in coupling phase with the allele of OL4 gene conferring resistance to PM and nematodes and the allele of TY1 gene conferring resistance to TYLCV on chromosome 6, wherein:
said allele of the OL4 gene conferring resistance to PM and nematodes is identified by SSR-OL4 marker detection,
said allele of the TY/gene conferring resistance to TYLCV is identified by TO-0178067 and/or TY3-M3 marker detection, and
the presence or absence of the allele of the Mi-1 gene conferring resistance to nematodes is identified by Mi2.3 marker detection,
wherein SSR-OL4 marker detection is performed by amplification, and detection of an amplification product of 382 bp, referred to as "allele of 382 bp" of the marker SSR-OL4, when using primers consisting of SEQ ID NO: 1 and SEQ ID NO: 2 indicates presence of the allele of the OL4 gene conferring resistance to PM and nematodes, and detection of an amplification product of 389 bp, referred to as "allele of 389 bp" of the marker SSR-OL4, when using primers consisting of SEQ ID NO: 1 and SEQ ID NO: 2 indicates absence of the allele of the OL4 gene conferring resistance to PM and nematodes;
wherein TO-0178067 marker detection is performed by amplification, and detection of an adenine (A) rather than a guanine (G) at position 247 of SEQ ID NO: 3 in an amplification product comprising sequence SEQ ID NO: 3, or in a fragment thereof including a G/A polymorphism at position 247 of SEQ ID NO: 3, referred to as "allele A" of the TO-0178067 marker, indicates the presence of the allele of the TY1 gene conferring resistance to TYLCV, and detection of a guanine (G) rather than an adenine (A) at position 247 of SEQ ID NO: 3 in an amplification product comprising sequence SEQ ID NO: 3, or in a fragment thereof including the G/A polymorphism at position 247 of SEQ ID NO: 3, referred to as "allele G" of the TO-0178067 marker, indicates the absence of the allele of the TY1 gene conferring resistance to TYLCV;
wherein TY3-M3 marker detection is performed by amplification, and detection of an amplification product of 220 bp, referred to as "allele of 220 bp" of the marker TY3-M3, when using primers consisting of SEQ ID NO: 7 and SEQ ID NO: 8 indicates presence of the allele of the TY/gene conferring resistance to TYLCV, and detection of an amplification product of 160 bp, referred to as "allele of 160 bp" of the marker TY3-M3, when using primers consisting of SEQ ID NO: 7 and SEQ ID NO: 8, indicates absence of the allele of the TY/gene conferring resistance to TYLCV; and
wherein Mi2.3 marker detection is performed by amplification, and detection of a cytosine (C) rather than a guanine (G) at position 88 of SEQ ID NO: 9 in an amplification product comprising SEQ ID NO: 9, or in a fragment thereof including a C/G polymorphism at position 88 of SEQ ID NO: 9, referred to as "allele C" of the marker Mi2.3, indicates the absence of the allele of the Mi-1 gene conferring resistance to nematodes, and detection of a guanine (G) rather than a cytosine (C) at position 88 of SEQ ID NO: 9 in an amplification product comprising SEQ ID NO: 9, or in a fragment thereof including the C/G polymorphism at position 88 of SEQ ID NO: 9, referred to as "allele G" of the marker Mi2.3, indicates the presence of the allele of the Mi-1 gene conferring resistance to nematodes.

2. The *S. lycopersicum* plant according to claim 1, which comprises one of the following combinations of alleles
Combination 1:
(i) the allele of 220 bp of the marker TY3-M3 and/or the "allele A" of the TO-0178067 marker, the allele of 382 bp of the marker SSR-OL4, and the "allele C" of the marker Mi2.3 physically located on the first homologous chromosome 6, and
(ii) the allele of 160 bp of the marker TY3-M3 and/or the "allele G" of the TO-0178067 marker, the allele of 389 bp of the marker SSR-OL4, and the "allele G" of the marker Mi2.3 physically located on the second homologous chromosome 6; or Combination 2:
(i) the allele of 220 bp of the marker TY3-M3 and/or the "allele A" of the TO-0178067 marker, the allele of 382 bp of the marker SSR-OL4, and the "allele C" of the marker Mi2.3 physically located on the first homologous chromosome 6, and
(ii) the allele of 160 bp of the marker TY3-M3 and/or the "allele G" of the TO-0178067 marker, the allele of 389 bp of the marker SSR-OL4, and the "allele C" of the marker Mi2.3 physically located on the second homologous chromosome 6; or Combination 3:
(i) the allele of 220 bp of the marker TY3-M3 and/or the "allele A" of the TO-0178067 marker, the allele of 382 bp of the marker SSR-OL4, and the "allele C" of the marker Mi2.3 physically located on the first homologous chromosome 6, and
(ii) the allele of 220 bp of the marker TY3-M3 and/or the "allele A" of the TO-0178067 marker, the allele of 382 bp of the marker SSR-OL4, and the "allele C" of the marker Mi2.3 physically located on the second homologous chromosome 6.

3. The *S. lycopersicum* plant according to claim 1, wherein said plant is the plant TCR1, a representative sample of seed of which has been deposited under NCIMB number 42490, or said plant is a plant having all of the morphological and physiological characteristics of plant TCR1.

4. The *S. lycopersicum* plant according to claim 1, wherein said plant is a progeny of a plant of line TCR1 a representative sample of seed of which has been deposited under NCIMB accession number 42490.

5. An isolated cell of the *S. lycopersicum* plant according to claim which comprises the (i) allele of the OL4 gene conferring resistance to PM and nematodes and (ii) the allele of the TY1 gene conferring resistance to TYLCV in coupling phase on chromosome 6, and wherein said cell, if it comprises the allele of the Mi-1 gene conferring resistance to nematodes then said allele of the Mi-1 gene conferring resistance to nematodes is not in coupling phase with the allele of the OL4 gene conferring resistance to PM and nematodes and allele of the TY1 gene conferring resistance to TYLCV on chromosome 6.

6. A plant part obtained from the *S. lycopersicum* plant as defined in claim 1, which comprises the (i) allele of the OL4 gene conferring resistance to PM and nematodes and (ii) allele of the TY1 gene conferring resistance to TYLCV in coupling phase on chromosome 6, and wherein said plant part, if it comprises the allele of the Mi-1 gene conferring resistance to nematodes then said allele of the Mi-1 gene conferring resistance to nematodes is not in coupling phase with the allele of the OL4 gene conferring resistance to PM and nematodes and allele of the TY1 gene conferring resistance to TYLCV on chromosome 6.

7. The plant part according to claim 6, wherein said plant part is a seed, a fruit, a parthenocarpic fruit, a reproductive material, roots, flowers, a rootstock or a scion.

8. A seed of a *S. lycopersicum* plant, giving rise when grown up to the plant according to claim 1.

9. A hybrid plant of a *S. lycopersicum*, which is resistant to Tomato Yellow Leaf Curl Virus (TYLCV), powdery mildew (PM) and nematodes obtained by crossing a *S. lycopersicum* plant with the *S. lycopersicum* resistant plant according to claim 1.

10. A method for identifying and selecting a *S. lycopersicum* plant that is resistant to Tomato Yellow Leaf Curl Virus (TYLCV), powdery mildew (PM) and nematodes, wherein said method comprises:

a) detecting
the presence or absence of an allele of the OL4 gene conferring resistance to PM and nematodes, said allele of the OL4 gene being identified by SSR-OL4 marker detection,
the presence or absence of an allele of the TY/gene conferring resistance to TYLCYV, said allele of TY/gene being identified by TO-0178067 and/or TY3-M3 marker detection, and
the presence or absence of an allele of the Mi-1 gene conferring resistance to nematodes, said allele of Mi-1 gene being identified by Mi2.3 marker detection; and b) selecting as a plant resistant to TYLCV, PM and nematodes the *S. lycopersicum* plant in which the allele of the OL4 gene conferring resistance to PM and nematodes and the allele of the TY1 gene conferring resistance to TYLCV have been detected as present in coupling phase on chromosome 6 and the allele of the Mi-1 gene conferring resistance to nematodes has been detected as absent in said coupling phase on chromosome 6, wherein SSR-OL4 marker detection is performed by amplification, and detection of an amplification product of 382 bp, referred to as "allele of 382 bp" of the marker SSR-OL4, when using primers consisting of SEQ ID NO: 1 and SEQ ID NO: 2 indicates presence of the allele of the OL4 gene conferring resistance to PM and nematodes, and detection of an amplification product of 389 bp, referred to as "allele of 389 bp" of the marker SSR-OL4, when using primers consisting of SEQ ID NO: 1 and SEQ ID NO: 2 indicates absence of the allele of the OL4 gene conferring resistance to PM and nematodes;

wherein TO-0178067 marker detection is performed by amplification, and detection of an adenine (A) rather than a guanine (G) at position 247 of SEQ ID NO: 3 in an amplification product comprising sequence SEQ ID NO: 3, or in a fragment thereof including a G/A polymorphism at position 247 of SEQ ID NO: 3, referred to as "allele A" of the TO-0178067 marker, indicates the presence of the allele of the TY1 gene conferring resistance to TYLCV, and detection of a guanine (G) rather than an adenine (A) at position 247 of SEQ ID NO: 3 in an amplification product comprising sequence SEQ ID NO: 3, or in a fragment thereof including the G/A polymorphism at position 247 of SEQ ID NO: 3, referred to as "allele G" of the TO-0178067 marker, indicates the absence of the allele of the TY1 gene conferring resistance to TYLCV;

wherein TY3-M3 marker detection is performed by amplification, and detection of an amplification product of 220 bp, referred to as "allele of 220 bp" of the marker TY3-M3, when using primers consisting of SEQ ID NO: 7 and SEQ ID NO: 8 indicates presence of the allele of the TY1 gene conferring resistance to TYLCV, and detection of an amplification product of 160 bp, referred to as "allele of 160 bp" of the marker TY3-M3, when using primers consisting of SEQ ID NO: 7 and SEQ ID NO: 8, indicates absence of the allele of the TY1 gene conferring resistance to TYLCV; and wherein Mi2.3 marker detection is performed by amplification, and detection of a cytosine (C) rather than a guanine (G) at position 88 of SEQ ID NO: 9 in an amplification product comprising SEQ ID NO: 9, or in a fragment thereof including a C/G polymorphism at position 88 of SEQ ID NO: 9, referred to as "allele C" of the marker Mi2.3, indicates the absence of the allele of the Mi-1 gene conferring resistance to nematodes, and detection of a guanine (G) rather than a cytosine (C) at position 88 of SEQ ID NO: 9 in an amplification product comprising SEQ ID NO: 9, or in a fragment thereof including the C/G polymorphism at position 88 of SEQ ID NO: 9, referred to as "allele G" of the marker Mi2.3, indicates the presence of the allele of the Mi-1 gene conferring resistance to nematodes.

11. The method according to claim 10, wherein:
amplification of the marker TO-0178067 is performed using two forward primers, one being specific for detecting the susceptible allele and consisting of the sequence 5'-GAAGGTGACCAAGTT-CATGCTTTTGTTCCCCCAGCTGAGAGG-3' (SEQ ID NO: 4) and one being specific for detecting the resistant allele and consisting of the sequence 5'-GAAGGTCGGAGTCAACGGAT-TCTTTTGTTCCCCCAGCTGAGAGA-3' (SEQ ID NO: 5), and a common reverse primer consisting of the sequence 5'-GACCAACACGKCCTACGAGGTA-3' (SEQ ID NO: 6),
amplification of the TY3-M3 marker is performed using a forward primer consisting of the sequence 5'-AGC-TATCAGCTGCCAGAGACAT-3' (SEQ ID NO: 7) and a reverse primer consisting of the sequence 5'-CAC-CATCATTGTATCCAGAGAGC-3' (SEQ ID NO: 8), and
amplification of the Mi2.3 marker is performed using two forward primers, one being specific for detecting the resistant allele and consisting of the sequence 5'-GAAGGTCGGAGTCAACGGATTCGACG-GAACTATTAAGTAGACGAG-3' (SEQ ID NO: 10) and one being specific for detecting the susceptible allele and consisting of the sequence 5'-GAAGGTGACCAAGTTCATGCTCGACGGAAC-TATTAAGTAGACGAC-3' (SEQ ID NO: 11), and a common reverse primer consisting of the sequence 5'-AACTGMTTTGGTTGCTTGTTATTTTACTAA-3' (SEQ ID NO: 12).

12. A method for obtaining *S. lycopersicum* plant resistant to Tomato Yellow Leaf Curl Virus (TYLCV), powdery mildew (PM) and nematodes which comprises crossing a *S. lycopersicum* that is resistant to Tomato Yellow Leaf Curl Virus (TYLCV), powdery mildew (PM) and nematodes, wherein said plant comprises (i) an allele of the OL4 gene conferring resistance to PM and nematodes and (ii) an allele of the TY/gene conferring resistance to TYLCV in coupling phase on chromosome 6, and wherein said plant, if it comprises an allele of the Mi-1 gene conferring resistance to nematodes, then said allele of the Mi-1 gene conferring resistance to nematodes is not in coupling phase with the allele of the OL4 gene conferring resistance to PM and nematodes and the allele of the TY1 gene conferring resistance to TYLCV on chromosome 6, with another *S. lycopersicum* plant, wherein:
said allele of the OL4 gene conferring resistance to PM and nematodes is identified by SSR-OL4 marker detection,
said allele of the TY1 gene conferring resistance to TYLCV is identified by TO-0178067 and/or TY3-M3 marker detection, and
the presence or absence of the allele of the Mi-1 gene conferring resistance to nematodes is identified by Mi2.3 marker detection,
wherein SSR-OL4 marker detection is performed by amplification, and detection of an amplification product of 382 bp, referred to as "allele of 382 bp" of the marker SSR-OL4, when using primers consisting of SEQ ID NO: 1 and SEQ ID NO: 2 indicates presence of the allele of the OL4 gene conferring resistance to PM and nematodes, and detection of an amplification product of 389 bp, referred to as "allele of 389 bp" of the marker SSR-OL4, when using primers consisting of SEQ ID NO: 1 and SEQ ID NO: 2 indicates absence of the allele of the OL4 gene conferring resistance to PM and nematodes;
wherein TO-0178067 marker detection is performed by amplification, and detection of an adenine (A) rather than a guanine (G) at position 247 of SEQ ID NO: 3 in an amplification product comprising sequence SEQ ID NO: 3, or in a fragment thereof including a G/A polymorphism at position 247 of SEQ ID NO: 3, referred to as "allele A" of the TO-0178067 marker, indicates the presence of the allele of the TY1 gene conferring resistance to TYLCV, and detection of a guanine (G) rather than an adenine (A) at position 247 of SEQ ID NO: 3 in an amplification product comprising sequence SEQ ID NO: 3, or in a fragment thereof including the G/A polymorphism at position 247 of SEQ ID NO: 3, referred to as "allele G" of the TO-0178067 marker, indicates the absence of the allele of the TY1 gene conferring resistance to TYLCV;
wherein TY3-M3 marker detection is performed by amplification, and detection of an amplification product of 220 bp, referred to as "allele of 220 bp" of the marker TY3-M3 when using primers consisting of SEQ ID NO: 7 and SEQ ID NO: 8 indicates presence of the allele of the TY1 gene conferring resistance to TYLCV, and detection of an amplification product of 160 bp, referred to as "allele of 160 bp" of the marker TY3-M3, when using primers consisting of SEQ ID NO: 7 and SEQ ID NO: 8, indicates absence of the allele of the TY/gene conferring resistance to TYLCV; and
wherein Mi2.3 marker detection is performed by amplification, and detection of a cytosine (C) rather than a guanine (G) at position 88 of SEQ ID NO: 9 in an amplification product comprising SEQ ID NO: 9, or in a fragment thereof including a C/G polymorphism at position 88 of SEQ ID NO: 9, referred to as "allele C" of the marker Mi2.3, indicates the absence of the allele of the Mi-1 gene conferring resistance to nematodes, and detection of a guanine (G) rather than a cytosine (C) at position 88 of SEQ ID NO: 9 in an amplification product comprising SEQ ID NO: 9, or in a fragment thereof including the C/G polymorphism at position 88 of SEQ ID NO: 9, referred to as "allele G" of the marker Mi2.3, indicates the presence of the allele of the Mi-1 gene conferring resistance to nematodes.

\* \* \* \* \*